United States Patent [19]
Bower et al.

[11] Patent Number: 6,086,558
[45] Date of Patent: Jul. 11, 2000

[54] BALLOON CATHETER FOR PHOTODYNAMIC THERAPY

[75] Inventors: Robert David Bower, Richmond; Michael David Leslie Stonefield; Joseph Yan, both of Vancouver, all of Canada

[73] Assignee: QLT PhotoTherapeutics, Inc., Canada

[21] Appl. No.: 09/222,474

[22] Filed: Dec. 29, 1998

Related U.S. Application Data

[63] Continuation of application No. 08/649,439, May 17, 1996, Pat. No. 6,013,053.

[51] Int. Cl.⁷ .................................................. A61M 29/00
[52] U.S. Cl. ............................ 604/96; 604/20; 604/500; 606/192; 607/88; 607/92
[58] Field of Search ................................ 604/96, 19–21, 604/500; 606/7, 8, 13–17, 192; 607/80, 88, 89, 92; 128/633, 634

[56] References Cited

U.S. PATENT DOCUMENTS

| | | | |
|---|---|---|---|
| 4,998,930 | 3/1991 | Lundahl | 606/15 |
| 5,041,109 | 8/1991 | Abela | 606/15 |
| 5,125,925 | 6/1992 | Lundahl | 606/15 |
| 5,169,395 | 12/1992 | Narcisco | 606/7 |
| 5,344,419 | 9/1994 | Spears | 606/15 |
| 5,354,293 | 10/1994 | Beyer et al. | 606/15 |
| 5,415,654 | 5/1995 | Daikuzono | 606/15 |
| 5,607,419 | 3/1997 | Amplatz et al. | 606/7 |
| 6,013,053 | 1/2000 | Bower et al. | 604/96 |

FOREIGN PATENT DOCUMENTS

| | | |
|---|---|---|
| 0 311 458 | 4/1989 | European Pat. Off. . |
| 0 411 132 | 2/1991 | European Pat. Off. . |
| 0 448 004 | 9/1991 | European Pat. Off. . |
| 9000420 | 1/1990 | WIPO . |
| 9000914 | 2/1990 | WIPO . |

OTHER PUBLICATIONS

Allardice, J.T. et al., "A new light delivery system for the treatment of obstructing gastrointestinal cancers by photodynamic therapy," *Gastrointestinal Endoscopy* 35(6):548–551 (Nov./Dec. 1989).

Marcus, S.L., "Photodynamic Therapy of Human Cancer: Clinical Status, Potential, and Needs," *Future Directions and Applications in Photodynamic Therapy/SPIE Institute Series vol. IS* 6:5–56 (1990).

Nseyo, U.O. et al., "Whole Bladder Photodynamic Therapy: Critical Review of Present–Day Technology and Rationale for Development of Intravesical Laser Catheter and Monitoring System," *Urology* 36(5):398–402 (Nov. 1990).

Overholt, B.F. et al., "Photodynamic Therapy in Barrett's Esophagus: Reduction of Specialized Mucosa, Ablation of Dysplasia, and Treatment of Superficial Esophageal Cancer," *Seminars in Surgical Oncology* 11(5):372–376 (Sep./Oct. 1995).

Overholt, B.F. et al., "Photodynamic Therapy for Esophageal Cancer Using a 180° Windowed Esphageal Balloon," *Lasers in Surgery and Medicine* 14(1):27–33 (1994).

Panjehpour, M. et al., "Centering Balloon to Improve Esophageal Photodynamic Therapy," *Lasers in Surgery and Medicine* 12(6):631–638 (1992).

*Primary Examiner*—John D. Yasko
*Attorney, Agent, or Firm*—Morrison & Foerster, LLP

[57] ABSTRACT

The present invention provides improved balloon catheter apparatuses for use in therapies requiring delivery of uniform light to a treatment area. The improved apparatus comprises a balloon having a defined treatment window where the window is delineated using a reflective material. The apparatus may further comprise a fiber optic cable that terminates in a diffusion tip where the diffusion tip is longer than the treatment window. The present invention further provides improved therapeutic methods that use the improved balloon catheters of the present invention.

19 Claims, 17 Drawing Sheets

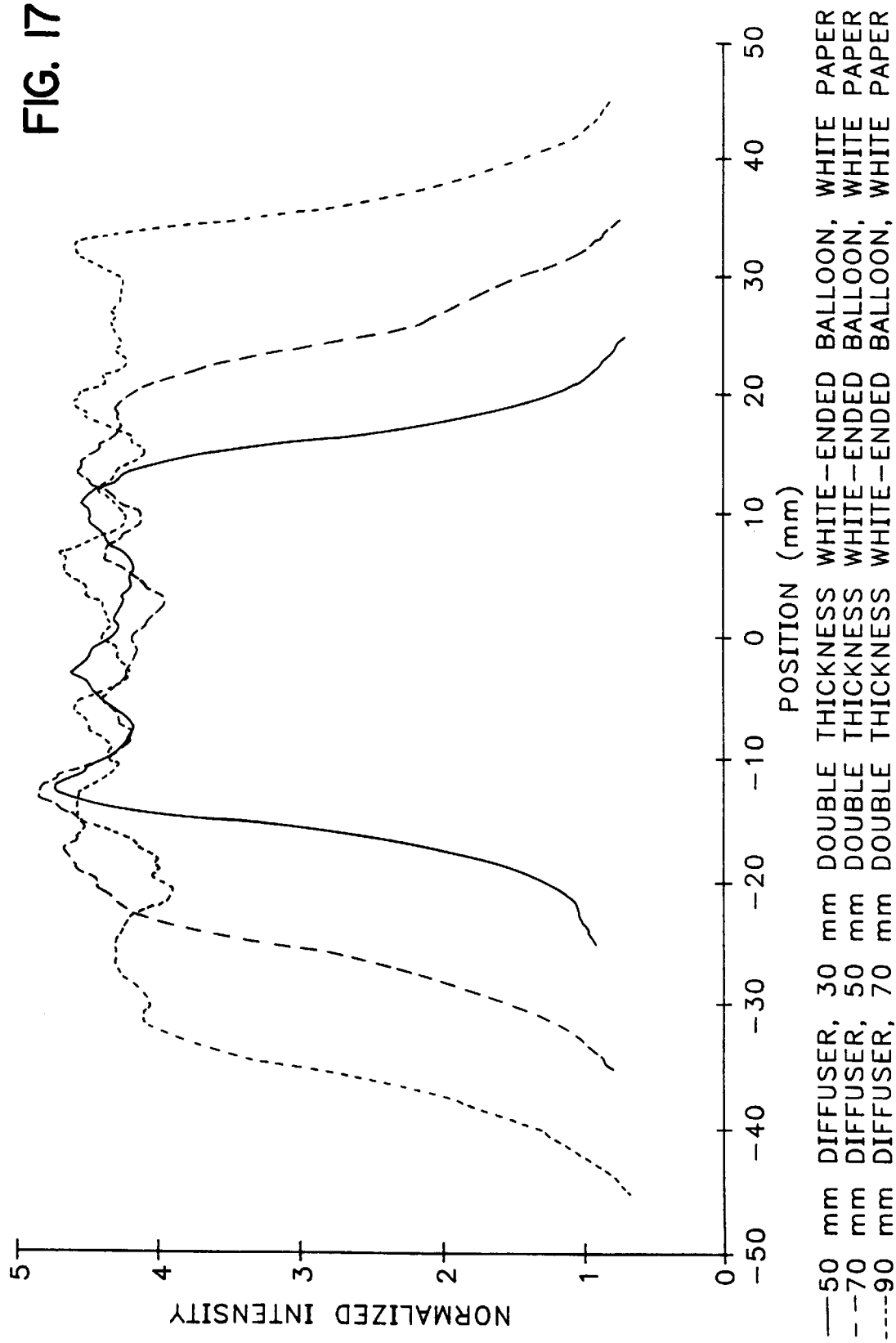

BALLOON CATHETER FOR PHOTODYNAMIC THERAPY

This application is a continuation of Ser. No. 08/649,439 filed May 17, 1996 now U.S. Pat. No. 6,013,053.

TECHNICAL FIELD

The present invention is in the field of medical devices used in administering light to a location within the body of a patient, such as in photodynamic therapy (PDT). The present invention provides improved balloon catheter devices that more evenly distribute light throughout the area of a treatment window.

BACKGROUND ART

There are a variety of medical procedures that require light or irradiated energy to be administered to a patient within the body. One example is therapeutic methods that use a light activated compound to selectively kill target cells in a patient, termed photoactivated chemotherapy. Other examples include optical diagnostic methods, hypothermia treatment and biostimulation. In photoactivated chemotherapeutic methods, a light-sensitive drug is injected into a patient and a targeted light source is used to selectively activate the light-sensitive drug. When activated by light of a proper wavelength, the light-sensitive drug produces a cytotoxic agent that mediates the destruction of the surrounding cells or tissue.

The main application of photoactivated therapy, such as PDT, is for the destruction of malignant cell masses. Photoactivated therapy has been used effectively in the treatment of a variety of human tumors and precancerous conditions including basal and squamous cells, skin cancers, breast cancer, metastatic to skin, brain tumors, head and neck, stomach, and the female genital tract malignancy, the cancers and precancerous conditions of the esophagus such as Barrett's esophagus. A review of the history and progress of photoactivated therapy is provided by Marcus, S. Photodynamic Therapy of Human Cancer: Clinical Status, Potential, and Needs. In Gomer, C. J. (ed.); "Future Directions and Applications in Photodynamic Therapy." Bellingham, W. A. SPIE Optical Engineering Press (1990) pp 5–56 and specific applications of PDT are provided by Overholt et al., *Sem. Surg. Oncol.* 11:1–5 (1995).

One area of focus in the development of phototherapeutic methods and apparatus is the development of targeted light sources that provide uniform illumination to a given treatment area.

Allardice et al. *Gastrointestinal Endoscopy* 35:548–551 (1989) and Rowland et al. PCT application WO 90/00914, disclose one type of light delivery systems designed for use with PDT. The disclosed system involves a flexible tube comprising a dilator and a transparent treatment window that defines a treatment area by using opaque end-caps made of stainless steel. A fiber optic element that is connected to a laser and ends in a diffusing tip is used in combination with the dilator to deliver light to a tissue source. Allardice et al. discloses the advantages of this apparatus over the use of balloon-type catheters in providing a more uniform distribution of light.

Nseyo et al. *Urology* 36:398–402 (1990) and Lundahl, U.S. Pat. Nos. 4,998,930 and 5,125,925, disclose a balloon catheter device for providing uniform irradiation to the inner walls of hollow organs. The device is based on a balloon catheter design and includes a balloon at one end of the apparatus and an optical fiber ending in a diffusion tip that is inserted into the lumen of the balloon through the catheter. The use of the catheter's centering tube was disclosed as providing a more uniform distribution of the laser light by centering the optical fiber in the inflated balloon. The catheter devices disclosed in these references further incorporate optical sensing fibers in the balloon wall to provide means for measuring illumination. However, there is no disclosure about the use of specific coating materials on the balloon to improve light uniformity or the use of a long diffusion tip that is longer than a delineated treatment window.

Panjehpour et al. *Lasers and Surgery in Medicine* 12:631–638 (1992) discloses the use of a centering balloon catheter to improve esophageal photodynamic therapy. Panjehpour discloses a cylindrical balloon catheter into which a fiber optic probe ending in a light diffuser is inserted. The cylindrical balloon containing the catheter is transparent and is not modified with a reflective coating to improve the diffusion of light within the balloon or to define a treatment window.

Overholt et al. *Lasers and Surgery in Medicine* 14:27–33 (1994) discloses modified forms of the balloon catheter device described by Panjehpour. The cylindrical balloon catheter was modified by coating both ends of the balloon with a black opaque coating to define a 360 degree treatment window. Overholt additionally describes a modified balloon in which one-half of the circumference of the treatment window is rendered opaque to light using the black coating material. This configuration provides a 180° treatment window. The black color guard used in the balloon to define the target window was not a reflective material and did not increase the uniformity of the light passing through the treatment window.

Rowland et al. PCT application WO 90/00420, discloses a light-delivery system for irradiating a surface. The device comprises a hemispherical shell whose inside is entirely coated with a diffuse reflector and a light source that is mounted within the shell. The light source may contain a diffusing source at the tip allowing diffusion of light within the reflective shell.

Spears, U.S. Pat. No. 5,344,419, discloses apparatuses and methods for making laser-balloon catheters. Spears utilizes a process that etches an end of a fiber optic cable to provide a diffusion tip on the optical cable. The optical cable containing the etched tip is secured within a central channel of a balloon catheter using a coating of adhesive containing microballoons. The position of the tip within the central channel and the microballoons contained in the adhesive provide increased efficiency in diffusing the laser radiation in a cylindrical pattern, providing a more uniform illumination at the target site.

Beyer, et al. U.S. Pat. No. 5,354,293 discloses a balloon catheter apparatus for delivering light for use in PDT. The balloon catheter device disclosed employs a conical tipped fiber optic cable to provide means of deflecting a light beam radially outward through a transparent portion of an inflated catheter.

In summary, there have been numerous devices that have been developed for use in PDT that employ a balloon catheter to support a light source in an ideal central point within a target area that is to be illuminated (Spears, Overholt, Beyer, Lundahl and Allardice) The main benefits of using a centering type balloon are that 1) the clinician does not have to hold the fiber optic in the central location, this is done automatically by the balloon catheter, 2) the light dose is more uniform across the entire treatment area than would be the case of light delivered by a fiber optic that is held central to the treatment volume without the aid of a balloon (while this is true with existing designs of balloon catheters, it is herein demonstrated that the uniformity can be significantly improved), 3) the treatment field is kept clean of contaminants e.g. blood, urine that might absorb the light and so affect the final PDT result, and 4) the overall treatment procedure can be considerably shortened as it is simpler setting up the fiber optic and getting the light dose correct. However, the disadvantage of using current cylindrical centering balloons with existing fiber optic diffusers is the inability to obtain uniform light being transmitted through the balloon to the target site.

Although each of the above disclosures provides means for providing light to a target site, there is no suggestion to use a reflective coating at the ends of a balloon catheter as a means of increasing both uniformity and efficiency in the distribution of the transmitted light. In addition, none of the devices employs a diffusing tip at the end of the fiber optic cable that is longer than the treatment window. These two features are present, alone or in combination, in the apparatus of the present invention and prove improved balloon catheter devices that more uniformly and efficiently distribute light over a treatment area.

SUMMARY OF THE INVENTION

The present invention provides improved balloon catheter apparatuses for use in therapeutic methods that require light illumination to a specific site. The improved apparatus comprises a balloon having a defined treatment window where the window is delineated using material that reflects and/or scatters light back towards the lumen of the balloon and zone defined as the treatment window. The apparatus may further comprise a fiber optic cable that terminates in a diffusion tip where the diffusion tip is longer than the treatment window.

The present invention further provides improved phototherapeutic methods that use the improved balloon catheters of the present invention.

BRIEF DESCRIPTION OF THE DRAWINGS

FIG. 17 shows scans of reflective coated catheters in which the length of the fiber active region is 2 cm longer than the balloon window.

DETAILED DESCRIPTION OF THE INVENTION

Figure 1A:
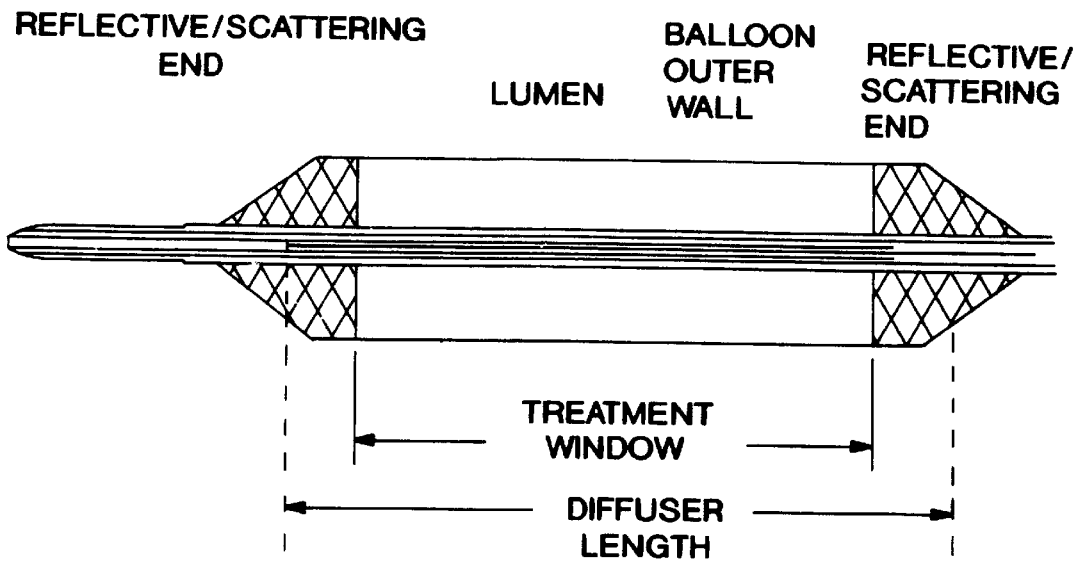
FIG. 1 provides a diagrammatic representation of the balloon components of the apparatus of the present invention. Panel A shows a balloon that provides a 360 degree treatment window. Panel B shows a balloon that provides a treatment window that is not 360 degrees.

The present invention provides improved balloon catheter devices for providing light irradiation to a defined area. Previous art-known balloon catheters, such as those disclosed by Overholt et al. *Lasers and Surgery in Medicine* 14:27–33 (1994), utilize an absorbing coating, such as black Color Guard supplied by Permatex Industrial Corp. Avon, Conn., on portions of the balloon to prevent the light from being transmitted through portions of the balloon. The non-blacked-out portions of the balloon thus define a treatment window that can be 360 degrees or can be segmented to be less than the entire circumference of the balloon, for example a 180 degree treatment window. It has been found that the intensity and overall uniformity of the light transmitted through the treatment window can be dramatically increased by using a coating that reflects and/or scatters light into the lumen of the balloon rather than the black absorbing coating used in the Overholt catheter.

Additionally, previously disclosed balloon catheter devices used in phototherapeutic methods employ a fiber optic cable ending in a diffusion tip that is centered in the balloon to provide even radial distribution of the light transmitted through the cable. The present invention improves on this configuration by disclosing that the intensity and overall uniformity of light transmitted through the treatment window can be increased by employing a diffusion tip that is longer than the treatment window.

Utilizing these observations, the present invention provides improved balloon catheters for use in providing light irradiation to a defined area. As used herein, light irradiation, light or irradiation, refers to light of wavelengths from about 300 nm to about 1200 nm. This includes UV, visible and infrared light. The choice of wavelength will be based on the intended use, namely being selected to match the activation wavelength of the photoactivated drug or the wavelength used for irradiation when a photoactivated compound is not employed. Examples of photoactivated compounds include, but are not limited to ALA, SnET2, phthalocyanines, BPD, PHOTOFRIN, MACE, psoralen, and derivatives thereof.

In one embodiment, the apparatus comprises an optically clear central channel into which a fiber optic probe can be inserted and an outer sleeve having a proximal end and a distal end and containing an inflatable balloon proximal to the distal end.

The balloon portion of the apparatus of the present invention can be manufactured to be any of a variety of shapes when inflated. Such shapes include, but are not limited to, spherical and cylindrical shapes with tapering ends. The preferred shape will depend on the shape and nature of the area of treatment. For example, when treating the esophageal tract, e.g., when treating Barrett's esophagus, a cylindrical shape with tapering ends is preferred.

The size and shape of the balloon and treatment will depend on the intended use. For example, when the device of the present invention is used to treat Barrett's esophagus, the preferred shape is cylindrical and will be from about 10 mm to about 200 mm in length and from about 10 mm to 35 mm in diameter when inflated. The diameter being selected to flatten the folds in the esophagus.

Any semi-resilient material that can form a balloon that can be inflated using either air or fluid can be used in making the balloon component of the present apparatus. The material can be either transparent or translucent. The preferred material will be transparent and non-distendable. The preferred material is a polyurethane membrane of a thickness of about 0.11 mm. However, any material that is used in the construction of other art known inflatable balloon catheters can readily be used in the devices of the present invention.

The balloon used in this embodiment of the apparatus of the present invention contains a reflective material that reflects and preferably also scatters light into the lumen and treatment window of the balloon. The material is contained on the ends of the balloon and the area that is not coated with the reflecting material defines a treatment area or window.

As used herein, a material is said to be reflective if the material prevents the transmission of light through the material by deflecting the light striking the material. The preferred material will also be able to scatter the deflected light, providing a diffuse reflection of the light hitting the material. The function of the reflective material is to provide increased uniformity and efficiency in the light transmitted through the treatment window and to prevent light from exposing non-target areas outside the treatment window.

Figure 1B:
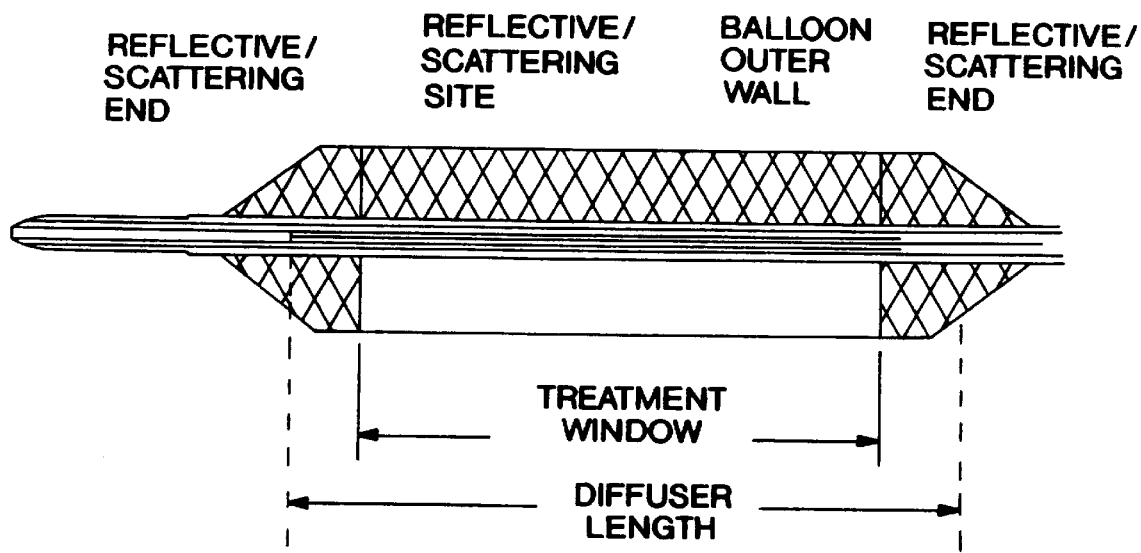
Figure 2:
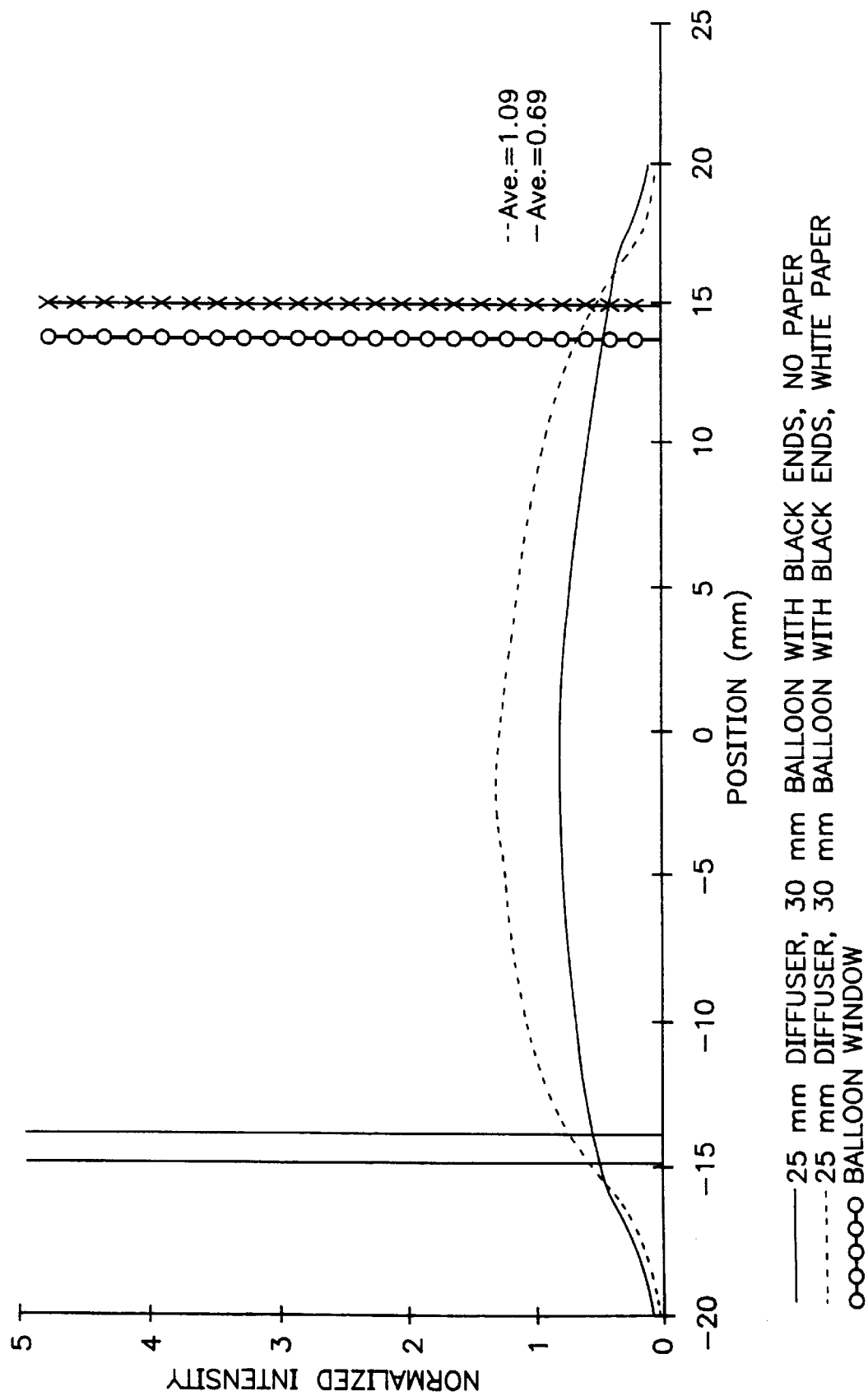
FIG. 2 shows scans of non-reflective, black-end coated catheters (Overholt catheter) having a 30 mm window using a fiber optic cable ending in a 25 mm diffuser, with and without white paper to simulate the effect of tissue scattering.
Figure 3:
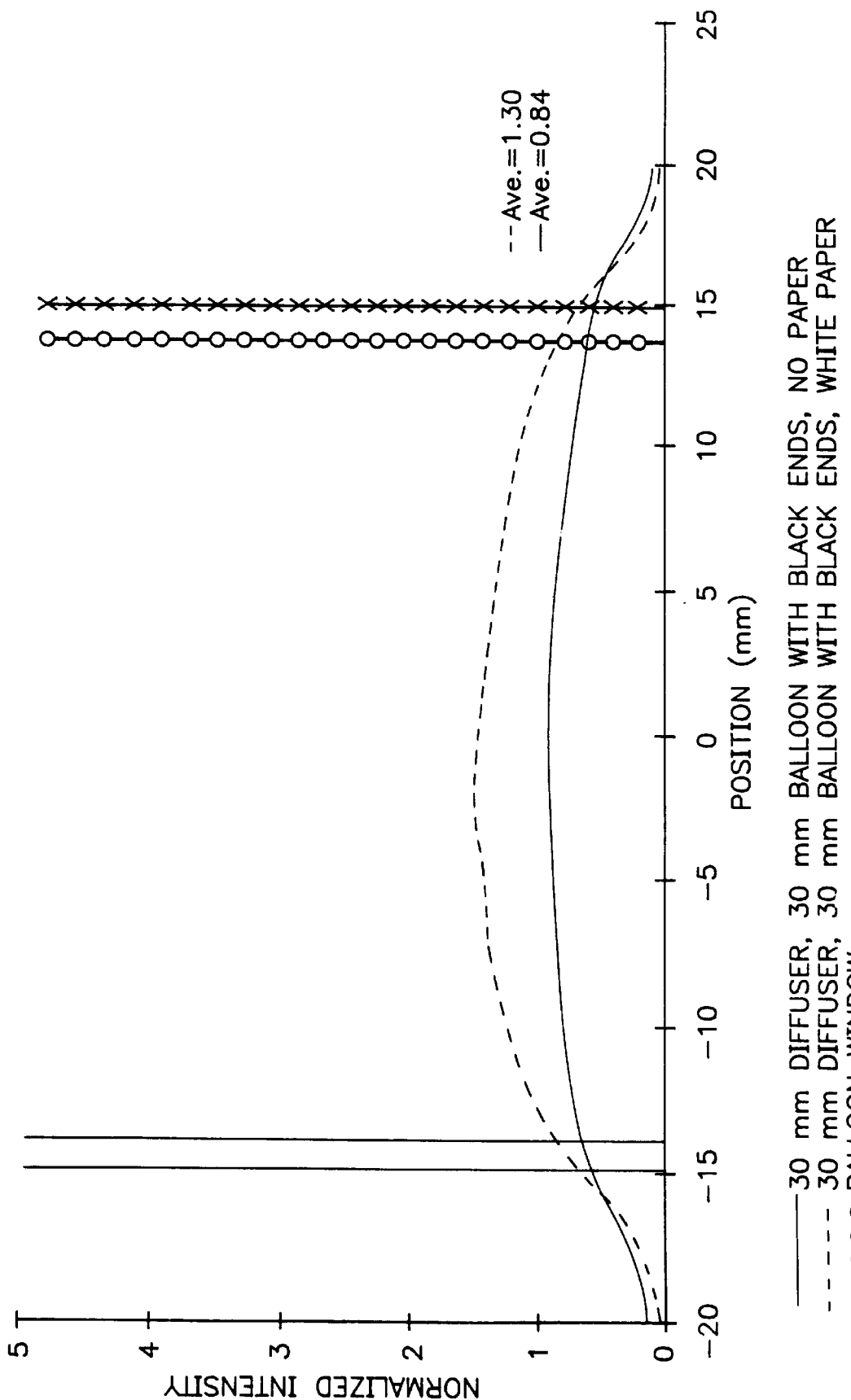
FIG. 3 shows scans of non-reflective, black-end coated catheters (Overholt catheter) having a 30 mm window using a fiber optic cable ending in a 30 mm diffuser, with and without white paper to simulate the effect of tissue scattering.
Figure 4:
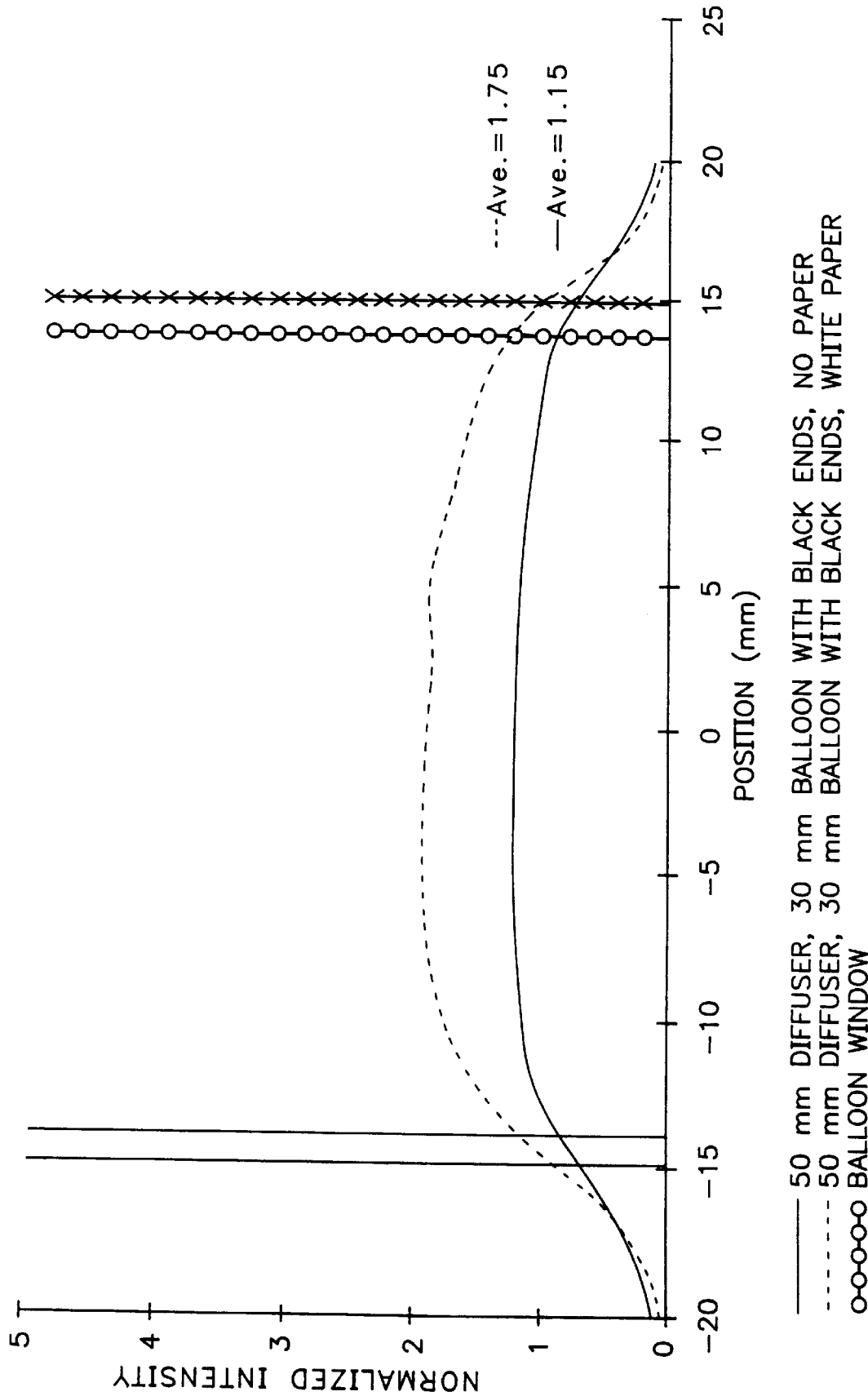
FIG. 4 shows scans of non-reflective, black-end coated catheters (Overholt catheter) having a 30 mm window using a fiber optic cable ending in a 50 mm diffuser, with and without white paper to simulate the effect of tissue scattering.
Figure 5:
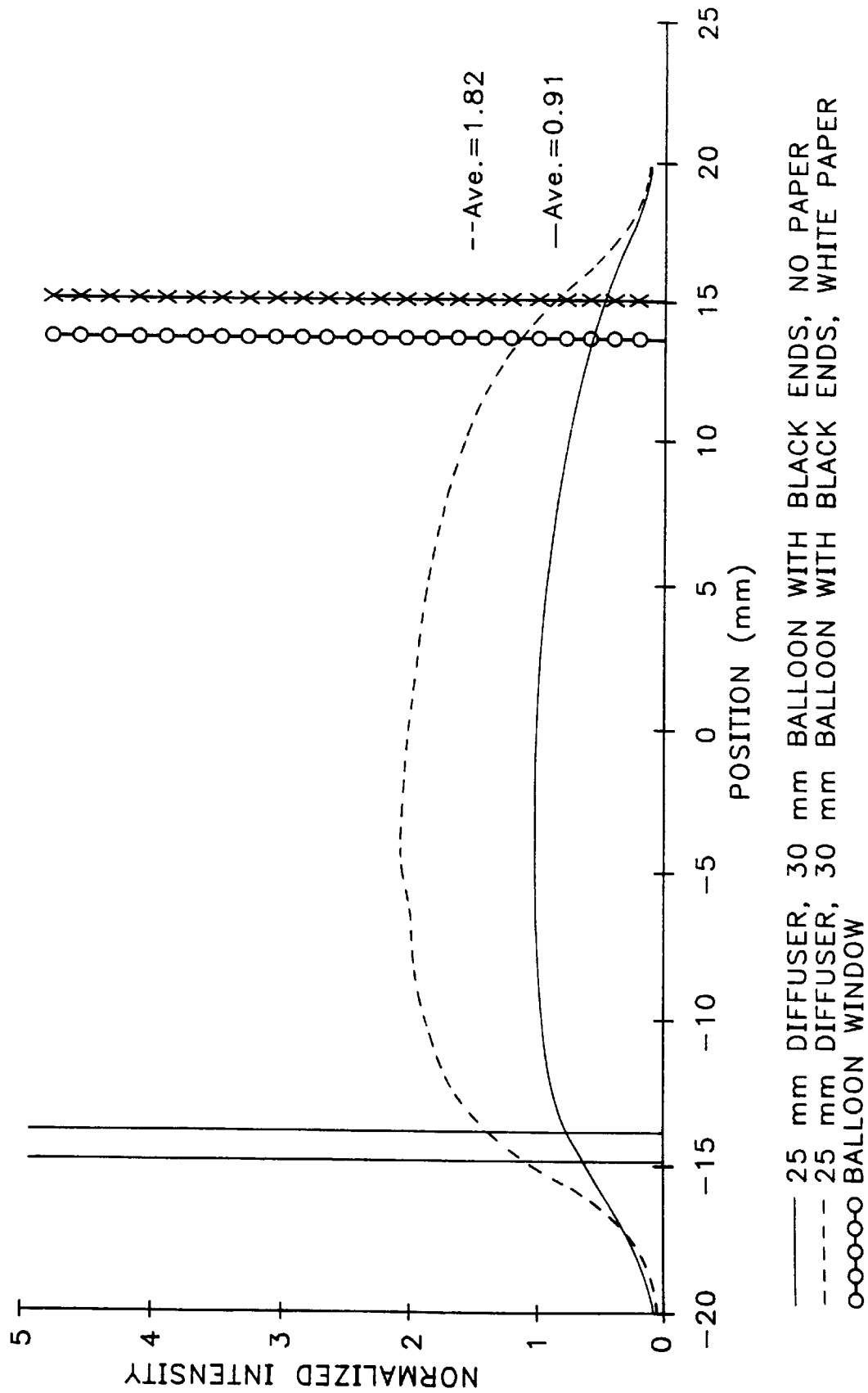
FIG. 5 shows scans of reflective, white-end coated catheters having a 30 mm window using a fiber optic cable ending in a 25 mm diffuser, with and without white paper to simulate the effect of tissue scattering.
Figure 6:
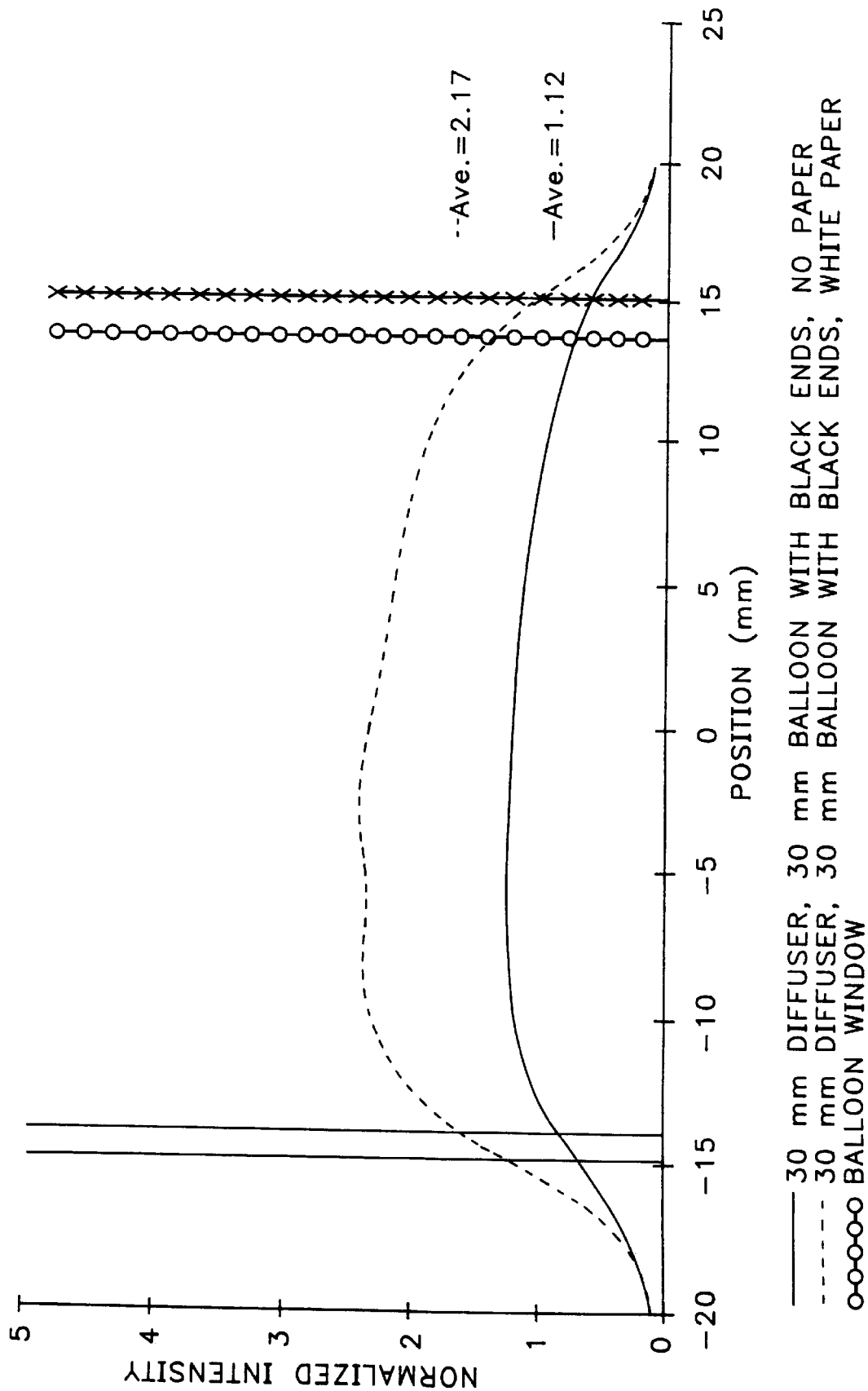
FIG. 6 shows scans of reflective, white-end coated catheters having a 30 mm window using a fiber optic cable ending in a 30 mm diffuser, with and without white paper to simulate the effect of tissue scattering.
Figure 7:
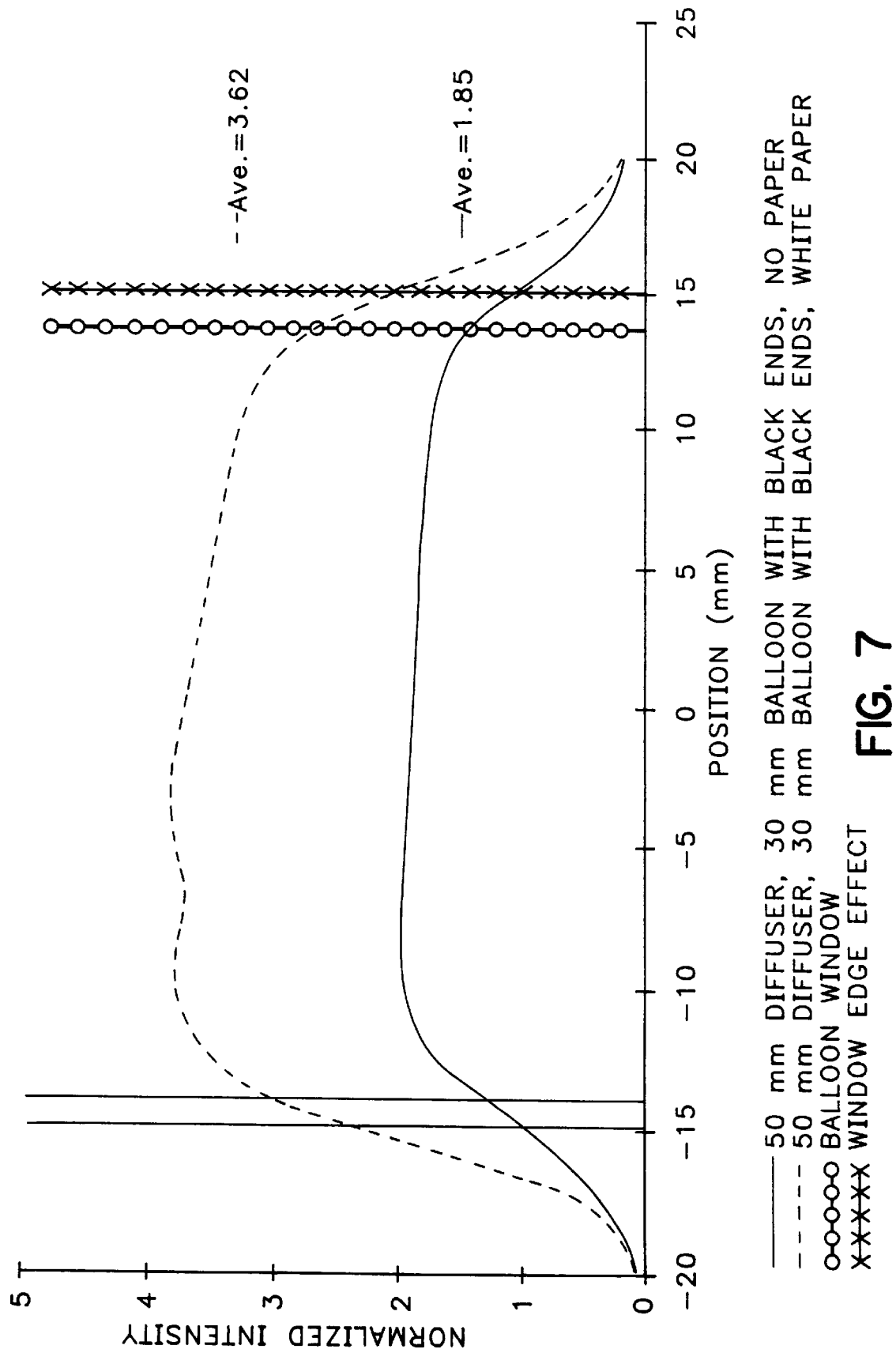
FIG. 7 shows scans of reflective, white-end coated catheters having a 30 mm window using a fiber optic cable ending in a 50 mm diffuser, with and without white paper to simulate the effect of tissue scattering.
Figure 8:
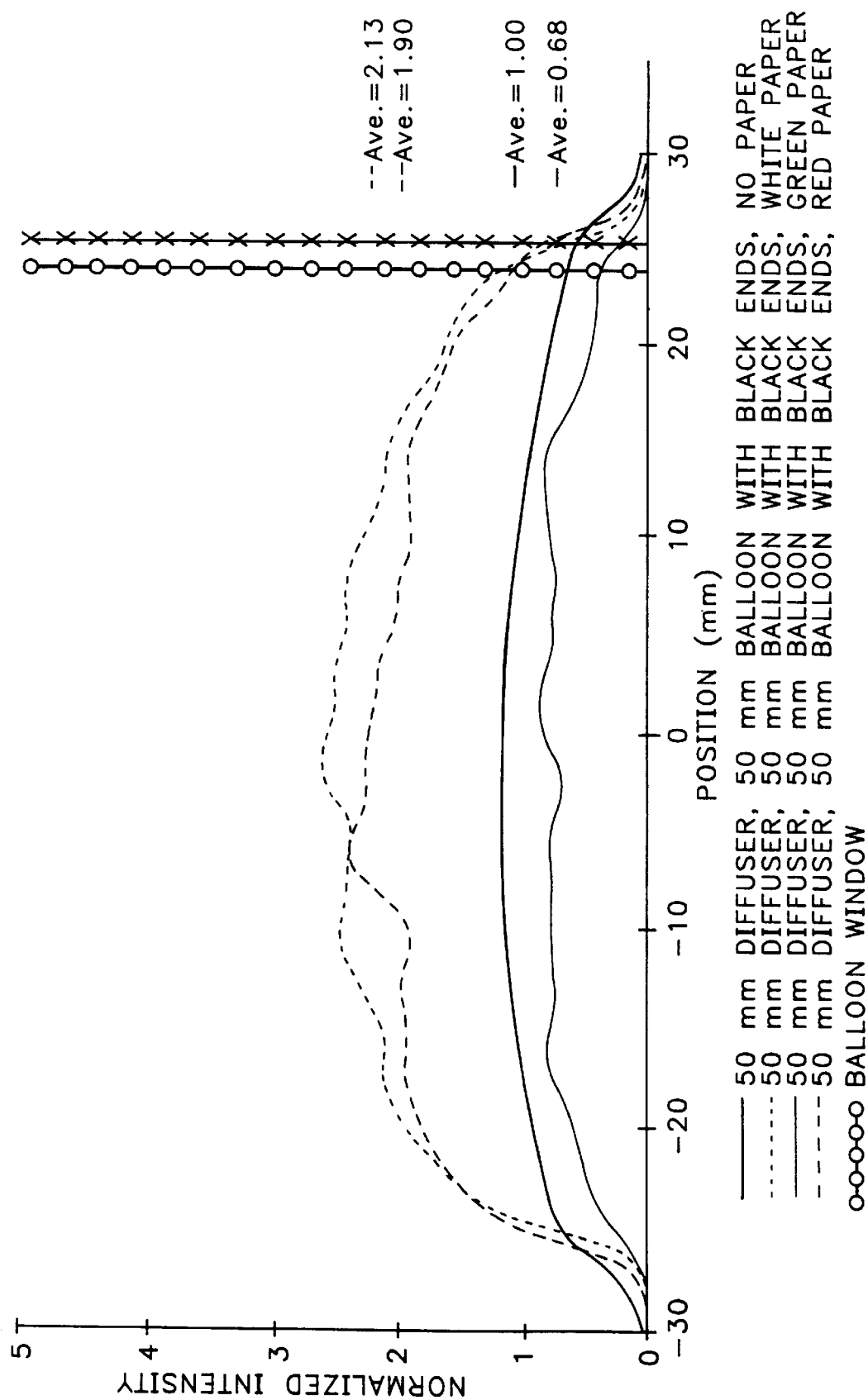
FIG. 8 shows scans of non-reflective, black-end coated catheters having a 50 mm window using a fiber optic cable ending in a 50 mm diffuser, with and without various colored paper to simulate the effect of tissue scattering.
Figure 9:
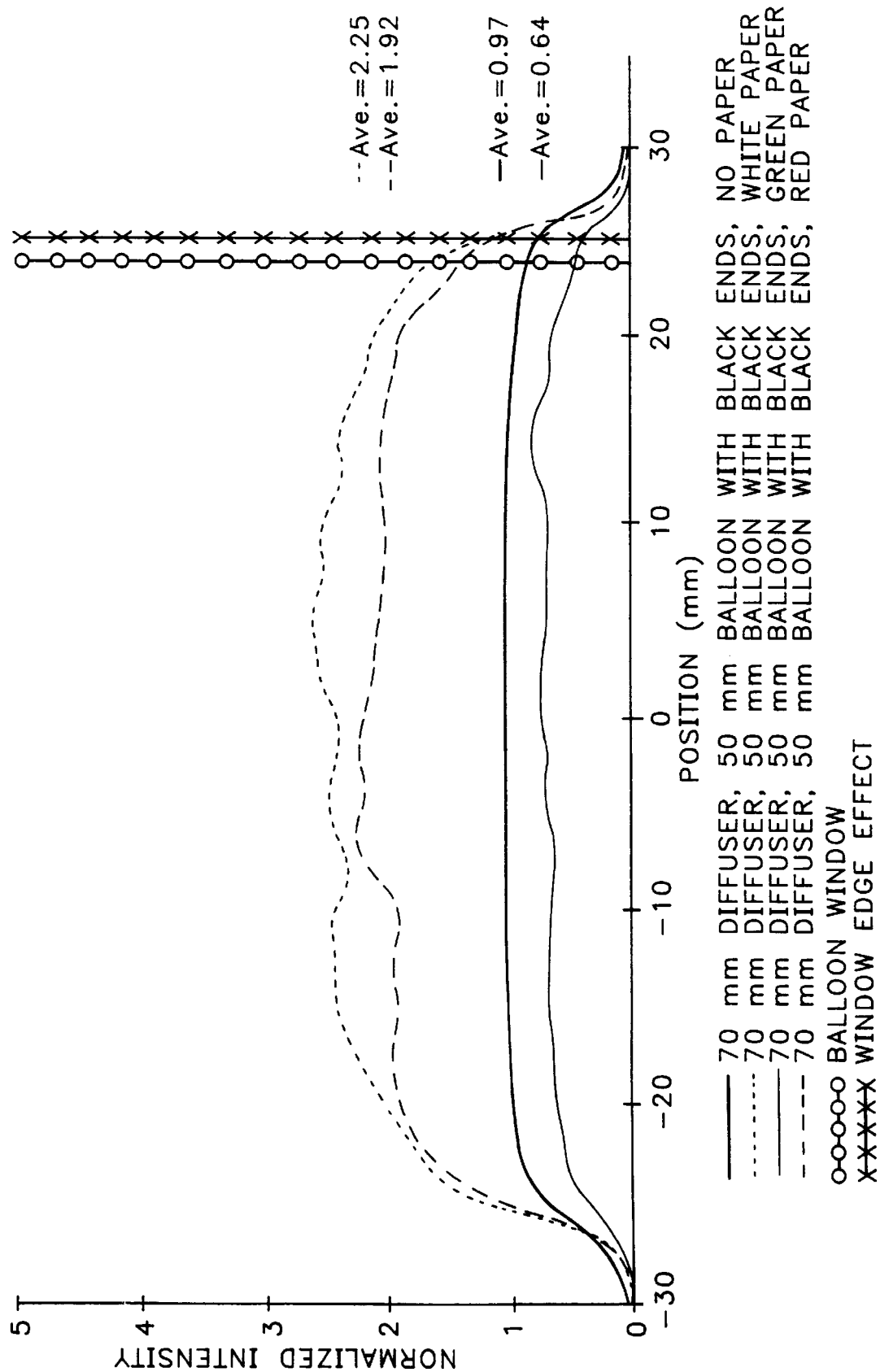
FIG. 9 shows scans of non-reflective, black-end coated catheters having a 50 mm window using a fiber optic cable ending in a 70 mm diffuser, with and without various colored paper to simulate the effect of tissue scattering.
Figure 10:
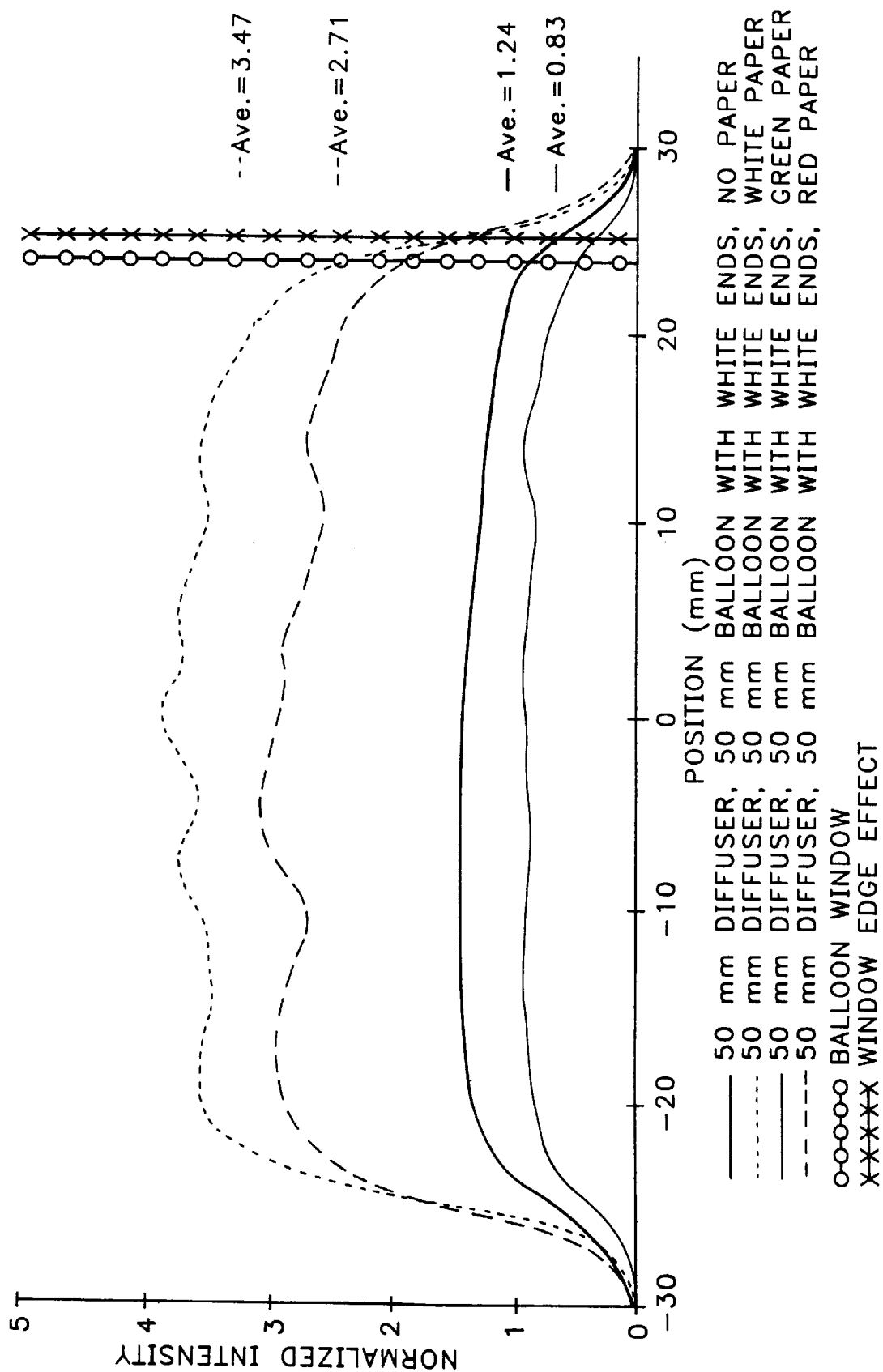
FIG. 10 shows scans of reflective, white-end coated catheters having a 50 mm window using a fiber optic cable ending in a 50 mm diffuser, with and without various colored paper to simulate the effect of tissue scattering.
Figure 11:
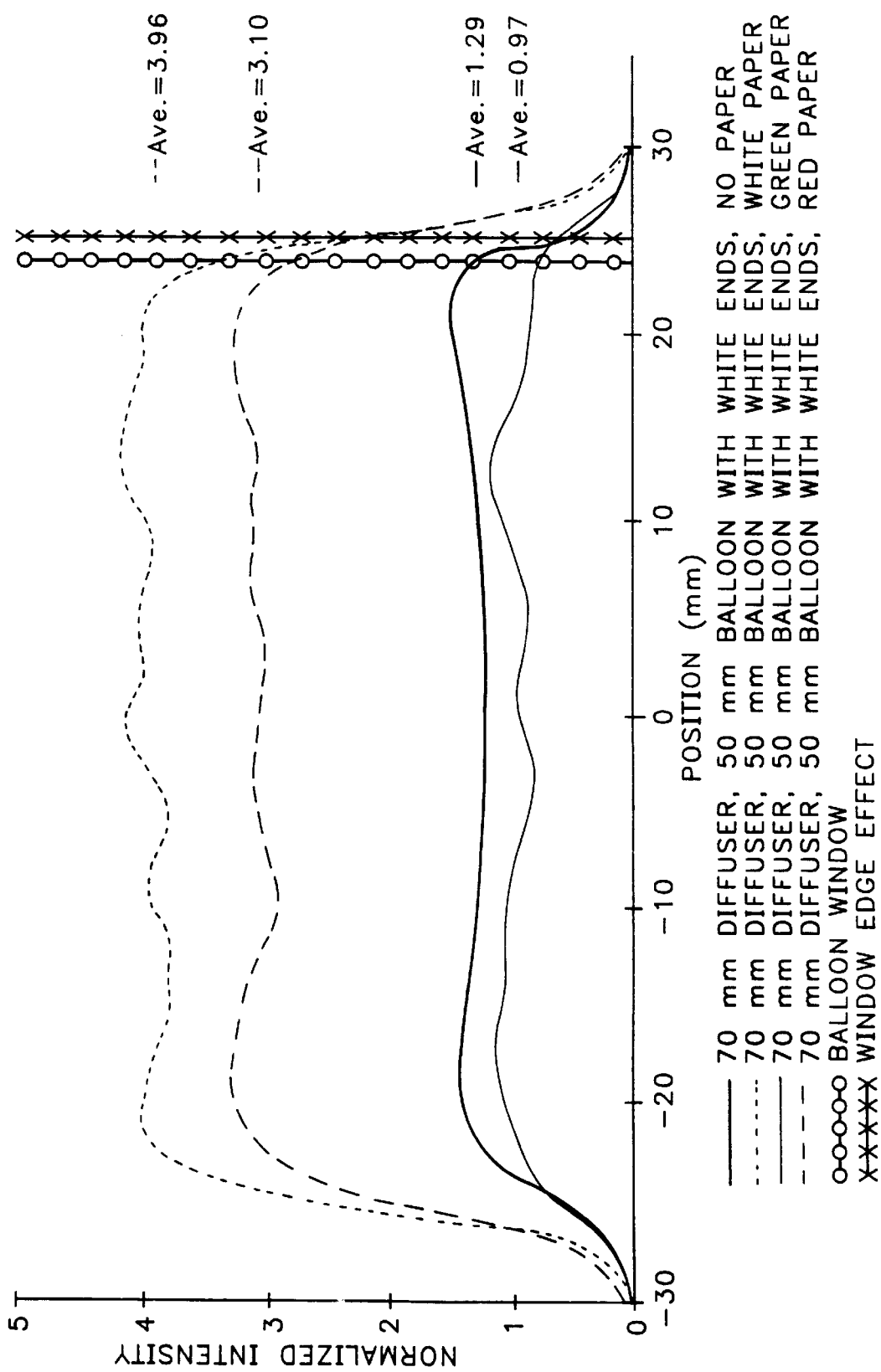
FIG. 11 shows scans of reflective, white-end coated catheters having a 50 mm window using a fiber optic cable ending in a 70 mm diffuser, with and without various colored paper to simulate the effect of tissue scattering.
Figure 12:
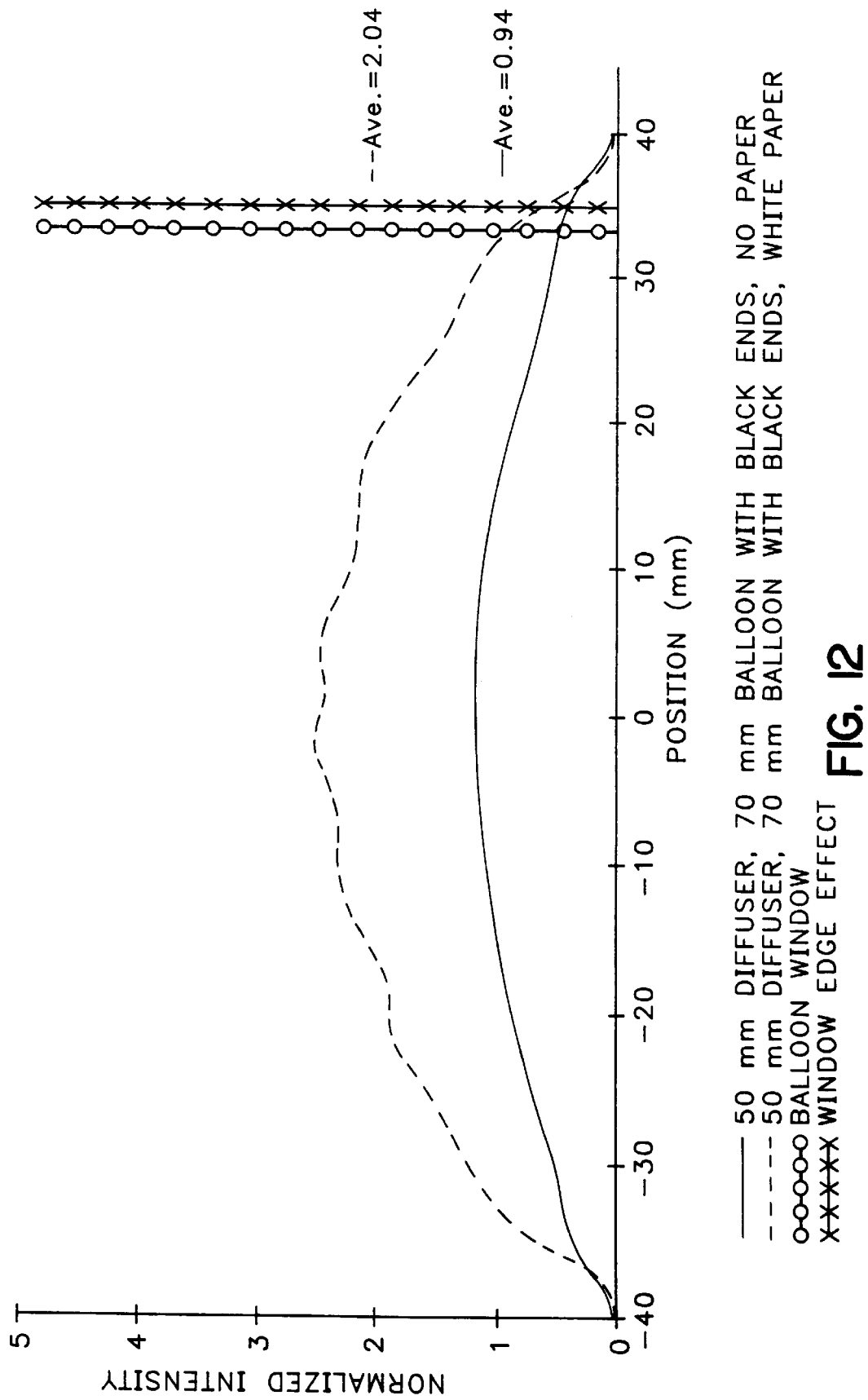
FIG. 12 shows scans of non-reflective, black-end coated catheters having a 70 mm window using a fiber optic cable ending in a 50 mm diffuser, with and without white colored paper to simulate the effect of tissue scattering.
Figure 13:
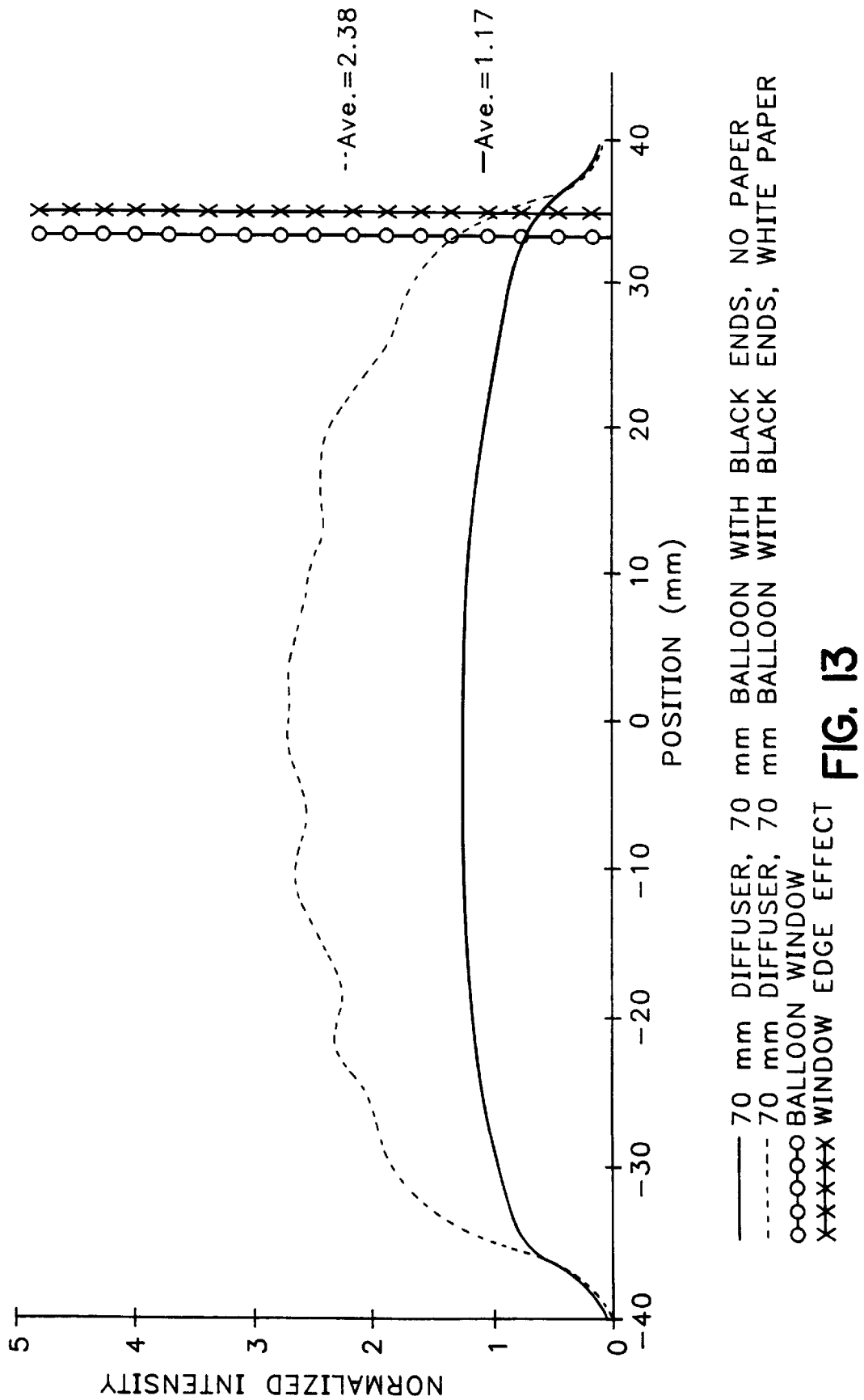
FIG. 13 shows scans of non-reflective, black-end coated catheters having a 70 mm window using a fiber optic cable ending in a 70 mm diffuser, with and without white colored paper to simulate the effect of tissue scattering.
Figure 14:
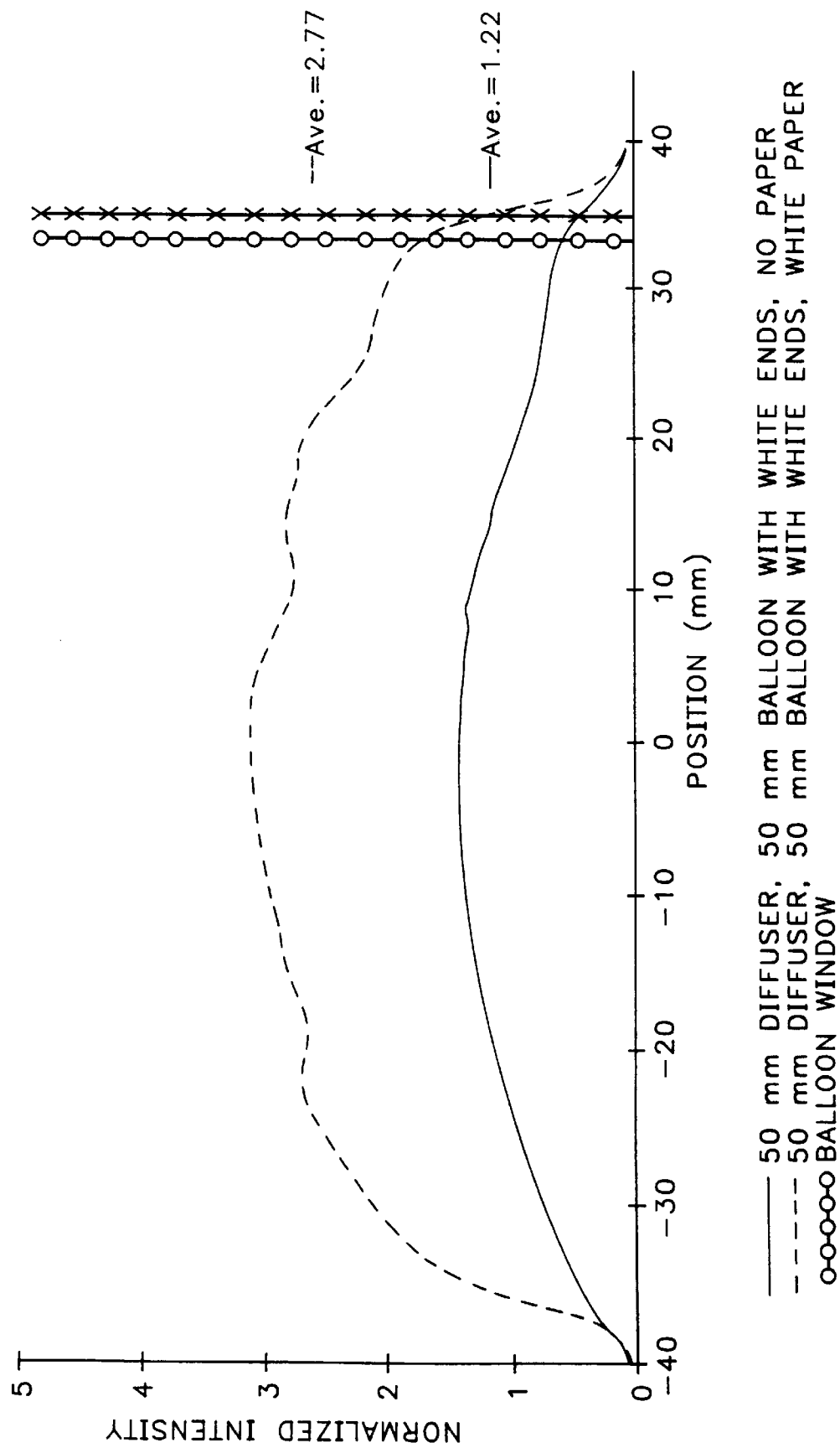
FIG. 14 shows scans of reflective, white-end coated catheters having a 70 mm window using a fiber optic cable ending in a 50 mm diffuser, with and without white colored paper to simulate the effect of tissue scattering.

FIG. 1 provides a diagrammatic representation of a balloon catheter that contains a reflective coating at both ends (panel a), or a reflective coating at both ends and a reflective coating over a portion of the circumference of the treatment window of the balloon (panel b).

Any coating material that is reflective, and in addition, can preferably scatter the reflected light, can be used as the reflective coating for the balloon component of this embodiment of the apparatus of the present invention. Examples of coating material include, but are not limited to, titanium dioxide, aluminum, gold, silver, and dielectric films. The choice of reflective material used will depend, in a large part, on the material used in the balloon, the method used to manufacture the balloon and the wavelength of light used in the phototherapy. A skilled artisan can readily adapt known reflective materials for incorporation into the balloon component of the apparatus of the present invention.

The preferred reflective material will reflect and scatter light and prevent from about 20% to 100% of light striking the material from passing through the material. The most preferred will reflect and scatter from about 70% to about 100% of the light.

The reflective material can be incorporated in the balloon component of the apparatus of the present invention in a variety of ways. For example, the reflective material can be applied to the surface of the balloon after the balloon is formed, for example by using a dipping process. Alternatively, the reflective material can be directly incorporated into the material used to form the balloon during the manufacturing of the balloon. The method used to incorporate the reflective material into the balloon will be based primarily on the reflective material used, the material the balloon is made of, and the method used to manufacture the balloon component. A skilled artisan can readily employ art-known procedures for incorporating a reflective material within or onto a surface of a balloon.

In addition to a reflective coating, the balloon component may further have an additional opaque coating over the reflective coating. An opaque coating is used to further prevent light from exiting the balloon outside the defined treatment window.

The balloon component may further contain optical sensors. Optical sensors that are integral to the balloon component can be used to measure the intensity of illumination when the catheter is used therapeutically. Optical sensors, such as a fiber optic probe or a photodiode as part of a balloon catheter, have been described in U.S. Pat. No. 5,125,925.

The apparatus of the present invention may further comprise a fiber optic cable, a fiber optic bundle or liquid light guide, for convenience, hereinafter referred collectively as a fiber optic cable. The fiber optic cable will contain one end that is readily attachable to a laser or non-laser light source and a second end onto which a diffuser is attached.

The light carrying section of the fiber optic cable, hereinafter the fiber optic core, can be of any diameter so long as the fiber optic cable can be inserted into the central channel of the balloon catheter. The preferred fiber optic core will be from about 50 to about 1000 microns in diameter, preferably about 400 microns. The choice of the core diameter will depend on the brightness of the light source and the optical power output required from the fiber optic diffuser tip.

As stated above, the fiber optic cable will terminate in a diffusion tip or diffuser. As used herein, a diffuser or diffusion tip, is defined as an element that can be attached to the end of a fiber optic cable, or a structure that can be formed at the end of the fiber optic cable, that provides a means for diffusing (scattering) the light being transmitted through the fiber optic cable so that it radiates outward from the fiber. Fiber optic diffusers are readily available and can be created by a variety of methods including, but not limited to, surrounding a central core with a scattering media or a scattering film, tapering the tip of the fiber optic cable to form a conical tip, or by inserting a tapered fiber optic tip into a cylindrical body containing optical scattering media. A variety of diffusion tips for using in PDT apparatus are described in U.S. Pat. Nos. 5,431,647, 5,269,777, 4,660,925, 5,074,632, and 5,303,324. The preferred diffusing tip for the fiber optic cable contained in the apparatus of the present invention is the cylindrical diffusion tip described in SBIR application grant 2R44CA60225/02 and available from Laserscope (CA).

The length of the diffusion tip can be varied relative to the size of the treatment window defined by the reflective material at the ends of the balloon component. It has been found that the intensity and uniformity of light being transmitted through the treatment window can be optimized by selecting a diffusion tip that is longer than the treatment window. Additionally, the longer diffusion tip eliminates the need for precise positioning of the fiber optic in the center of the treatment window In the Examples that follow, it was found that a diffusion tip that is longer than the treatment window provided an increase in the uniformity of light being transmitted through the treatment window. Preferably, the diffusion tip will extend from about 0.3 cm to about 5 cm on either side of the treatment window.

Recent developments in producing small efficient light emitting diodes (LEDs) permits the use of a probe having multiple LEDs mounted on an end to form a distributed array. Such a probe can replace the fiber optic cable and diffuser by being inserted, LED end first, into the central channel. The LEDs emit a diverging beam of light without the need for a diffuser, although a diffuser can be incorporated into such a probe to increase diffusion. In such a configuration, the LEDs cover the probe to a length equivalent to the diffuser tip and is equivalent to, and referred to as the fiber optic cable or probe.

In an alternative configuration, the balloon component can be provided without the optically clear central channel. In such a configuration, a fiber optic cable containing the diffusion tip is connected to the distal end of the balloon and is pulled to a central location when the balloon is inflated.

The catheters of the present invention can be used with any wavelength of light. The choice of the wavelength will be determined by the intended use. In the examples that follows, 633 nm wavelength light, supplied using a helium neon laser, was used. This is the activation wavelength for a variety of photoactivated compounds used in PDT. The choice of materials used in each of the components of the catheters of the present invention, and in particular the reflective coating and the overall geometry of the finished assembly, can be specifically tailored to provide the desired properties for a given treatment wavelength and indication being treated.

Each component of the improved balloon catheters of the present invention, namely the reflective coating and a diffusion tip that is longer than the treatment window, provides increased uniformity and efficiency in transmitting light to a defined treatment area. Each component can be used independently with presently available catheters, for example a longer tip can be used with an Overholt style catheter, or both components can be used in combination.

The present invention further provides improved methods for irradiating a surface with light. Specifically, the improved methods rely on the use of the balloon catheters of the present invention. The balloon catheters of the present invention are particularly useful in PDT for the treatment of malignancies of the esophagus, particularly Barrett's esophagus, for biostimulation and the treatment of hypothermia. The devices of the present invention can readily be used by a skilled artisan in all known phototherapeutic and illumination applications for which a balloon illumination catheter can be used.

The following examples are intended to illustrate but not to limit the invention. All of the cited references are herein incorporated by reference.

EXAMPLE 1

The following data provides a comparison of the present disclosed balloon catheters and balloon catheters essentially as described by Overholt et al. *Lasers and Surgery in Medicine* 14:27–33 (1994). The data summarizes studies performed using balloons with black ends (B) or reflective white ends (W) under condition with and without a simulated tissue reflector at the wall of the balloon (referred to either paper:none or paper:white). Additionally, a comparison of different balloon window length/fiber optic diffuser lengths is provided.

Data was collected using an automated scanning system that utilizes a modified UDT photodiode (Grasaby Optronics (FL)) as a detector essentially as described by Kozodoy, et al., *"New system for Characterising the Light Distribution of Optical Fiber Diffusers for PDT Application" Proc. SPIE OE/LASE* 2131A-16 (January 1994) and modified to collect linear scans for the purposes of these tests. Light of 633 nm wavelength was provided to the fiber optic probe using a helium neon laser (Aerotech, PA). The balloon catheters were supplied by Polymer Technology Group (CA). The optical diffuser tips were supplied by Laserscope (CA).

The data in this example was obtained by simulating a reflective end capped balloon by painting white liquid paper (Gillette (MA)) on the ends of a transparent PTG balloon. The data presented in Examples 2 and 3 used balloon catheters containing a reflective $TiO_2$ coating that were specifically manufactured by PTG.

FIGS. 2–15 summarize the data collected. Each figure shows one or more scans along the length of the balloon window for a variety of different parameters. The figures show the normalized light intensity/fluence rate (y-axis) plotted against the position along the balloon window (x-axis). All of the figures are plotted so that the y-axis from one figure to the other can be directly compared. The x-axis matches the balloon catheter window length (X=0 is the center of the treatment window).

As can be seen, the light intensity drops off as the detector starts to intersect the edges of the window ("window edge effect" zone). The point at which the intensity drops off in this zone is determined by the finite diameter of the detector (2 mm in this case). The 2 mm diameter factors in the averaging of light in tissue that results from scattering. For the purpose of analyzing the data and comparing it from one geometry to another, the section of the scan beyond the areas labeled as the "window edge effect" was ignored and only the central section of the scans were utilized. Each scan also has shown alongside it the average intensity, and the caption at the bottom identifies the parameters being investigated.

The figures can be split into 3 broad groups: FIGS. 2–7 show all the 30 mm balloon window data; FIGS. 8–11 show all the 50 mm balloon window data; FIGS. 12–15 show all the 70 mm balloon window data.

Tables 1 and 2 summarize the numbers that have been compiled from the data presented in FIGS. 2–15. Table 1 provides the data obtained with a fiber optic diffuser that matches the length of the balloon window while Table 2 provides the data obtained with a fiber optic diffuser that is 2 cm longer than the balloon window.

In addition to the basic description of the parameters being used and the average and standard deviation, both tables provide calculated values for the "goodness of uniformity". This is defined as the percentage of the scan length within a defined plus/minus band from the mean. A number of plus/minus tolerances (+10%, +20%, +30%) were deliberately chosen to see what impact this would have on the values calculated. The region that were of particular interest is the "Properly Treated Region" (PTR), and values approaching 1.0 were considered as being excellent (all power within tolerance limits), and numbers less than this having some power outside of the tolerances. PTR is meant to refer to whether the light with a local intensity within this tolerance will produce the desired PDT response in tissue.

One of the difficulties facing the development of effective PDT for treating disorders of the esophagus is that there is little information of how critical the light uniformity needs to be in phototherapeutic methods such as PDT treatment of Barrett's esophagus. However, it is reasonable to conclude that increased uniformity of transmitted light should yield a more even response in the treated area, potentially avoiding the need to retreat an given region. Based on the above, using the ±10% data in Tables 1 and 2 as the data that is used to determine the ideal balloon catheter and fiber optic geometry, with a nominal acceptance criteria of >0.70 as being a good value for the PTR, then the fiber optic balloon catheter configurations that meet typical clinical needs will 1) have a fiber optic diffusion tip that is approximately 2 cm longer than the treatment window and 2) will have reflecting end material that defines the limits of the treatment window.

An additional important characteristic relates to the average value of the intensity ($I_{av}$) for each balloon catheter/fiber optic combination measured at the balloon window. With reflective coated, white-end catheters and white paper around the balloon to simulate tissue scattering: a 3 cm window and 5 cm diffuser had a $I_{av}$=3.6; a 5 cm window and 5 cm diffuser had a $I_{av}$=3.5; a 7 cm window and 7 cm diffuser had a $I_{av}$=3.5; a 3 cm window and 5 cm diffuser had a $I_{av}$=3.6; and a 5 cm window and 7 cm diffuser had a $I_{av}$=4.0.

With no paper around the balloon to simulate tissue scattering: a 3 cm window and 5 cm diffuser had a $I_{av}$=1.8; a 5 cm window and 5 cm diffuser had a $I_{av}$=1.3; a 7 cm window and 7 cm diffuser had a $I_{av}$=1.3; a 3 cm window and 5 cm diffuser had a $I_{av}$=1.8; and a 5 cm window and 7 cm diffuser had a $I_{av}$=1.3.

For all the data given above, the power output from each length of fiber optic diffuser was normalized to a single power/cm output from the diffuser tip P, (mW/cm) so the $I_{av}$ data from the various combinations given above can be directly compared.

Within each data set (white paper vs. no white paper) the average values of $I_{av}$ are reasonably similar (to within ±10–20% of their mean). This implies that a single J/cm value can be set for each fiber optic, i.e., the clinician measures the power required according to a known mW/cm for each fiber optic.

The $I_{av}$ obtained for non-reflective, black-end coated catheters, using white paper to simulate tissue scattering: a 3 cm window and 2.5 cm diffuser had a $I_{av}$=1.1; and a 5 cm window and 5 cm diffuser had a $I_{av}$=2.1. With no paper to simulate tissue reflection: a 3 cm window and 2.5 cm diffuser had a $I_{av}$=0.7; and a 5 cm window and 5 cm diffuser had a $I_{av}$=1.0. (See Table 2).

Clinically, Overholt has found it necessary to use 250–300 J/cm for the 3 cm balloon and 125–150 J/cm for the 5 cm balloon (__). Overholt's light doses define a ratio of 1.67–2.4:1 (average of 2:1) for the different balloon catheters combinations he used. This is comparable to the values measured above by looking at ration calculated with and without white scattering paper, i.e., 1.4–2.0:1.

Another key point to note is that the average intensity measure above with the various geometry's are higher than those obtained using an Overholt catheter. This means, quite significantly, that where Overholt is using a light dose of about 275 J/cm with his 3 cm balloon, the present catheter would use only $$275 \times (1.1/3.6) = 84 \text{ J/cm}$$

to get the same clinical result and the same light dose (J/cm$^2$) at the tissue with any of the disclosed balloon lengths. This can be used as a benefit in two ways. With existing balloon catheters (black ended) 400 mW/cm is typically used, resulting in a treatment time of 11.5 minutes for 275 J/cm. With the reflective end balloon and diffuser tip that is longer than the treatment window, either the treatment time can be reduced (for example to 7 minutes at 200 mW/cm) or the mW/cm can be reduced to 84 mW/cm. The latter is extremely important since it would allow the use of inexpensive laser diodes, even when using a 9 cm diffuser (1.1 W laser diode needed assuming a 30% loss in the fiber optic).

Based on the above results, a balloon with white ends provides a more uniform light dose at tissue, and this together with an appropriate cylindrical diffuser length fiber optic will permit a single P1 (mW/cm) and E1 (J/cm) to be used for PDT treatment with all such balloon catheter/fiber optic combinations. An additional benefit is that the integration effect produced by the reflecting balloon ends allows for the reduction in the treatment time or the ability to use less expensive, lower power lasers.

In summary, extensive testing has shown that quite unexpectedly, by changing the ends of the Overholt Barrett's style balloon catheter from a black absorbing material to reflecting/scattering material, together with the use of fiber optics that overlap the treatment window, the uniformity of the light at the balloon surface is significantly improved. Prior to the present investigation of the optical characteristics of balloon catheters, it was assumed that opaque balloon catheter ends should be used simply to prevent the light from passing beyond the ideal treatment zone and it was believed that the light dosimetry would be similar for each balloon catheter irrespective of length. Recently Overholt and Panjehpour have collected clinical data that confirms the assumption that with a black ended balloon catheter, a single light dose EL cannot be used (__).

When the light field out of the balloon catheter with black ends was measured, it was observed that the light intensity decayed as the edges of the windows were approached, and so the black balloon ends were changed to a reflecting material. An improvement in the uniformity profile was observed, although the uniformity still dropped off at the ends. When the fiber optic diffuser was extended beyond the window length, a further improvement in the uniformity profile was observed. Using this configuration, it was possible to define a balloon catheter/fiber optic geometry that allows a single value of EL to be defined.

An additional surprising benefit was that the integration effect obtained with the catheters of the present invention is sufficiently great that low power lasers may now be usable in areas that were previously impossible. This opens up many opportunities for PDT as the need for costly high power lasers has been a significant limitation. In particular it is likely that laser diodes with a 1.5 W output and operating at 630 nm will now be usable to treat Barrett's esophagus, even though the currently planned treatment lengths are up to 7 cm long. Previously this would have been unthinkable as a means for delivering the light dose required for typical PDT methods since the treatment time would need to be about 1 hour using 3 to 4 treatment segments to cover the entire 7 cm length.

EXAMPLE 2

The following data was generated using reflective coated, $TiO_2$, white-ended balloons (provided by the Polymer Technology Group).

The results are presented in Table 3. The data has been normalized in such a way that it can be directly compared with the data provided in the previous examples.

Focusing on the scans generating using white paper to simulate tissue scattering of the administered light, the key factors to notice are:

1. The result confirm the results obtained in Example 1 using a balloon that incorporates a clinically viable scatter in the wall, namely $TiO_2$.
2. The mean average is roughly constant (4.34 to 4.44; a difference of only a few percent). Previously, the uncertainty about the variability in the integration factor was a cause for concern. The integration constant is also higher than for previous measurements (the ends have higher reflectivity).
3. The properly treated region (PTR) remains high—no less than 88.7%.
4. The coefficient of variation is low and roughly constant (the standard deviation is no greater than 7% of the mean).

This demonstrates that with a well thought out design, matching the reflectivity of the white ended balloons to the lengths, the mean average can be held constant irrespective of the balloon window length. The higher integration factor will help reduce the requirements of the light system used to deliver light to the fiber optic.

EXAMPLE 3

Figure 16:
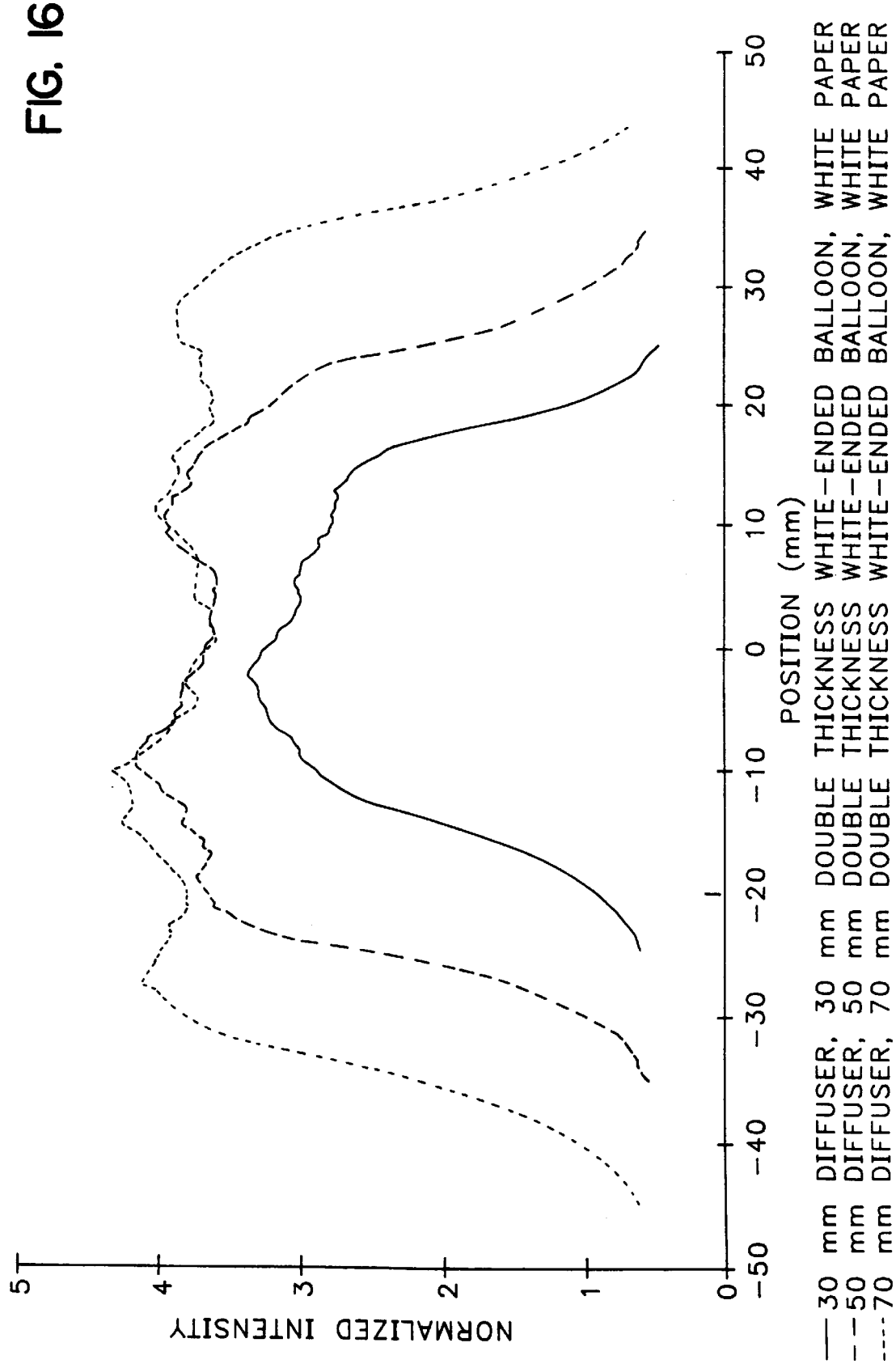
FIG. 16 shows scans of reflective coated catheters in which the length of the fiber active region and the balloon window are equivalent.

FIGS. 16 and 17 provide graphical scans that can be used to compare the uniformity of light through the treatment window obtained with different window size/diffuser size combinations. FIG. 16 shows the scans for cases in which the lengths of the diffuser and the balloon window are equivalent. FIG. 17 shows the scans for cases in which the length of the diffuser is 2 cm longer than the balloon window. Both scans were performed in the presence of a white scatter paper to simulate tissue scattering effects.

Figure 15:
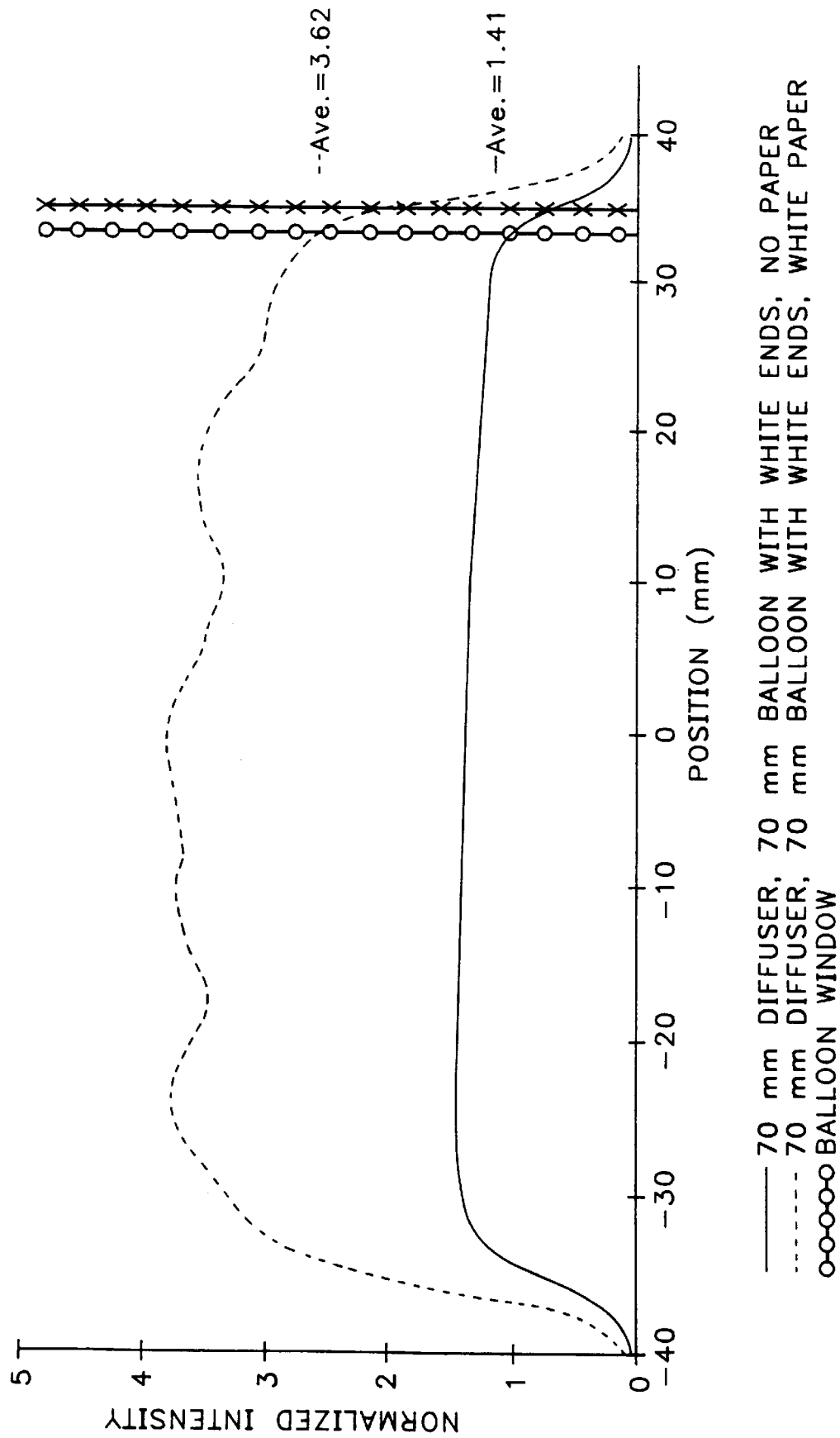
FIG. 15 shows scans of reflective, white-end coated catheters having a 70 mm window using a fiber optic cable ending in a 70 mm diffuser, with and without white colored paper to simulate the effect of tissue scattering.

The data present in FIGS. 15 and 16 are summarized in Table 3. Table 3 further contains a summary of results obtained when a white scatter paper was not used.

These result provided confirms and further supports the conclusions provided in Example 3, namely the advantages of using the longer fiber optics and a reflective coating.

TABLE 1

|  | T1 | T2 | T9 | T10 | T21 | T22 | T33 | T34 | T41 | T42 | T45 | T46 |
|---|---|---|---|---|---|---|---|---|---|---|---|---|
| Paper | None | White | None | White | None | White | None | White | None | White | None | White |
| Ends | B | B | W | W | B | B | W | W | B | B | W | W |
| Diffuser | 5 | 5 | 5 | 5 | 3 | 3 | 3 | 3 | 7 | 7 | 7 | 7 |
| Balloon | 5 | 5 | 5 | 5 | 3 | 3 | 3 | 3 | 7 | 7 | 7 | 7 |
| Mean Average | 1.000 | 2.149 | 1.295 | 3.494 | 0.839 | 1.290 | 1.121 | 2.161 | 1.116 | 2.272 | 1.347 | 3.463 |
| Standard Deviation | 0.147 | 0.362 | 0.133 | 0.291 | 0.099 | 0.187 | 0.146 | 0.279 | 0.146 | 0.391 | 0.098 | 0.314 |
| Coefficient of Variation | 0.147 | 0.169 | 0.103 | 0.083 | 0.118 | 0.145 | 0.130 | 0.129 | 0.130 | 0.172 | 0.073 | 0.091 |
| Max (as Prcnt of Mean) | 1.160 | 1.227 | 1.107 | 1.117 | 1.136 | 1.179 | 1.128 | 1.137 | 1.134 | 1.204 | 1.082 | 1.112 |
| Min (as Prcnt of Mean) | 0.635 | 0.536 | 0.674 | 0.640 | 0.712 | 0.637 | 0.649 | 0.610 | 0.634 | 0.536 | 0.670 | 0.668 |
| ** +/−30% ** | | | | | | | | | | | | |
| Undertreated Region | 0.041 | 0.073 | 0.007 | 0.011 | 0.000 | 0.042 | 0.032 | 0.032 | 0.022 | 0.072 | 0.004 | 0.007 |
| Overtreated Region | 0.000 | 0.000 | 0.000 | 0.000 | 0.000 | 0.000 | 0.000 | 0.000 | 0.000 | 0.000 | 0.000 | 0.000 |
| Properly Treated Region | 0.959 | 0.927 | 0.993 | 0.989 | 1.000 | 0.958 | 0.968 | 0.968 | 0.978 | 0.928 | 0.996 | 0.993 |
| ** +/−20% ** | | | | | | | | | | | | |
| Undertreated Region | 0.136 | 0.170 | 0.057 | 0.045 | 0.085 | 0.132 | 0.111 | 0.106 | 0.112 | 0.162 | 0.022 | 0.039 |
| Overtreated Region | 0.000 | 0.050 | 0.000 | 0.000 | 0.000 | 0.000 | 0.000 | 0.000 | 0.000 | 0.011 | 0.000 | 0.000 |
| Properly Treated Region | 0.864 | 0.780 | 0.943 | 0.955 | 0.915 | 0.868 | 0.889 | 0.894 | 0.888 | 0.827 | 0.978 | 0.961 |
| ** +/−10% ** | | | | | | | | | | | | |
| Undertreated Region | 0.261 | 0.247 | 0.181 | 0.109 | 0.222 | 0.238 | 0.222 | 0.206 | 0.235 | 0.283 | 0.077 | 0.173 |
| Overtreated Region | 0.367 | 0.429 | 0.073 | 0.043 | 0.270 | 0.291 | 0.317 | 0.323 | 0.325 | 0.364 | 0.000 | 0.042 |
| Properly Treated Region | 0.372 | 0.324 | 0.746 | 0.848 | 0.508 | 0.471 | 0.460 | 0.471 | 0.441 | 0.353 | 0.923 | 0.785 |

TABLE 2

|  | T5 | T6 | T13 | T14 | T17 | T18 | T25 | T26 | T29 | T30 | T37 | T38 |
|---|---|---|---|---|---|---|---|---|---|---|---|---|
| Paper | None | White | None | White | None | White | None | White | None | White | None | White |
| Ends | B | B | W | W | B | B | B | B | W | W | W | W |
| Diffuser | 7 | 7 | 7 | 7 | 2.5 | 2.5 | 5 | 5 | 2.5 | 2.5 | 5 | 5 |
| Balloon | 5 | 5 | 5 | 5 | 3 | 3 | 3 | 3 | 3 | 3 | 3 | 3 |
| Mean Average | 0.98 | 2.26 | 1.30 | 3.98 | 0.69 | 1.08 | 1.15 | 1.75 | 0.91 | 1.81 | 1.84 | 3.61 |
| Standard Deviation | 0.05 | 0.25 | 0.09 | 0.16 | 0.10 | 0.18 | 0.10 | 0.21 | 0.13 | 0.25 | 0.16 | 0.29 |
| Coefficient of Variation | 0.05 | 0.11 | 0.07 | 0.04 | 0.15 | 0.17 | 0.09 | 0.12 | 0.14 | 0.14 | 0.08 | 0.08 |
| Max (as Prcnt of Mean) | 1.05 | 1.15 | 1.14 | 1.07 | 1.17 | 1.21 | 1.09 | 1.12 | 1.14 | 1.15 | 1.09 | 1.09 |
| Min (as Prcnt of Mean) | 0.82 | 0.66 | 0.71 | 0.83 | 0.62 | 0.58 | 0.73 | 0.65 | 0.61 | 0.59 | 0.67 | 0.70 |
| ** +/−30% ** | | | | | | | | | | | | |
| Undertreated Region | 0.00 | 0.02 | 0.00 | 0.00 | 0.05 | 0.07 | 0.00 | 0.03 | 0.05 | 0.04 | 0.01 | 0.01 |
| Overtreated Region | 0.00 | 0.00 | 0.00 | 0.00 | 0.00 | 0.00 | 0.00 | 0.00 | 0.00 | 0.00 | 0.00 | 0.00 |
| Properly Treated Region | 1.00 | 0.98 | 1.00 | 1.00 | 0.95 | 0.93 | 1.00 | 0.97 | 0.95 | 0.96 | 0.99 | 0.99 |
| ** +/−20% ** | | | | | | | | | | | | |
| Undertreated Region | 0.00 | 0.08 | 0.01 | 0.00 | 0.12 | 0.16 | 0.04 | 0.10 | 0.12 | 0.12 | 0.05 | 0.04 |
| Overtreated Region | 0.00 | 0.00 | 0.00 | 0.00 | 0.00 | 0.07 | 0.00 | 0.00 | 0.00 | 0.00 | 0.00 | 0.00 |
| Properly Treated Region | 1.00 | 0.92 | 0.99 | 1.00 | 0.88 | 0.76 | 0.96 | 0.90 | 0.88 | 0.88 | 0.95 | 0.96 |
| ** +/−10% ** | | | | | | | | | | | | |
| Undertreated Region | 0.06 | 0.18 | 0.02 | 0.02 | 0.26 | 0.28 | 0.16 | 0.21 | 0.23 | 0.22 | 0.12 | 0.12 |
| Overtreated Region | 0.00 | 0.16 | 0.09 | 0.00 | 0.36 | 0.38 | 0.00 | 0.19 | 0.35 | 0.29 | 0.00 | 0.00 |
| Properly Treated Region | 0.94 | 0.66 | 0.89 | 0.96 | 0.38 | 0.35 | 0.84 | 0.60 | 0.41 | 0.49 | 0.88 | 0.88 |

TABLE 3

New Data Using PTG Double-Thickness White-Ended Balloons (25% TIO2 Loading)

| File Name | 53WE | 75WE | 97WE | 53NE | 75NE | 97NE | 33WE | 55WE | 77WE | 33NE | 55NE | 77NE |
|---|---|---|---|---|---|---|---|---|---|---|---|---|
| Fiber Length (cm) | 5 | 7 | 9 | 5 | 7 | 9 | 3 | 5 | 7 | 3 | 5 | 7 |
| Balloon Length (cm) | 3 | 5 | 7 | 3 | 5 | 7 | 3 | 5 | 7 | 3 | 5 | 7 |
| Scattering Paper | White | White | White | None | None | None | White | White | White | None | None | None |
| Mean Average | 4.44 | 4.34 | 4.37 | 1.74 | 1.50 | 1.35 | 2.99 | 3.70 | 3.85 | 1.17 | 1.26 | 1.20 |
| Standard Deviation | 0.16 | 0.31 | 0.23 | 0.11 | 0.21 | 0.17 | 0.27 | 0.33 | 0.26 | 0.09 | 0.11 | 0.19 |
| Coefficient of Variation | 0.04 | 0.07 | 0.05 | 0.06 | 0.14 | 0.13 | 0.09 | 0.09 | 0.07 | 0.07 | 0.09 | 0.16 |
| Max (as Prcnt of Mean) | 107.9% | 113.1% | 109.9% | 111.3% | 130.3% | 132.6% | 113.8% | 113.7% | 113.1% | 106.4% | 110.7% | 136.1% |
| Min (as Prcnt of Mean) | 93.0% | 70.6% | 78.4% | 73.9% | 53.0% | 52.3% | 72.2% | 66.6% | 68.8% | 67.5% | 58.7% | 63.8% |
| ** +/−10% ** | | | | | | | | | | | | |
| Undertreated Region | 0.0% | 6.2% | 3.8% | 3.5% | 23.7% | 3.6% | 10.5% | 13.4% | 5.8% | 8.8% | 7.2% | 33.6% |
| Overtreated Region | 0.0% | 5.2% | 0.0% | 7.0% | 23.7% | 16.8% | 15.8% | 8.2% | 4.4% | 0.0% | 3.1% | 24.1% |
| Properly Treated Region | 100.0% | 88.7% | 96.4% | 89.5% | 52.6% | 79.6% | 73.7% | 78.4% | 89.8% | 91.2% | 89.7% | 42.3% |

What is claimed is:

1. An apparatus for providing irradiation to a defined area, said apparatus comprising a balloon catheter having a defined treatment window comprising:

i) a clear central channel into which a fiber optic probe can be inserted; and ii) an outer sleeve, for use in inflating a balloon, having a proximal end and a distal end, said sleeve further containing an inflatable balloon proximate to said distal end; wherein said balloon is coated on both ends with a reflective material so as to define a treatment window.

2. The apparatus of claim 1 wherein said treatment window is from about 1 cm to about 20 cm in length.

3. The apparatus of claim 1 wherein the treatment window in said balloon is cylindrical in shape.

4. The apparatus of claim 3 wherein said cylindrical treatment window is from about 3 mm to about 200 mm in length and from about 1 mm to 100 mm in diameter when inflated.

5. The apparatus of claim 1 wherein said reflective coating is selected from the group consisting of $TiO_2$, aluminum, silver or gold.

6. The apparatus of claim 1 further comprising a fiber optic cable that terminates in diffuser, said diffuser being longer than said treatment window.

7. The apparatus of claim 6, wherein said diffuser is a cylindrical diffuser.

8. The apparatus of claim 7 wherein said diffuser is about 2 cm longer than said treatment window.

9. The apparatus of claim 1 wherein said balloon is made of high density polyurethane.

10. The apparatus of claim 1 wherein said treatment window is transparent.

11. The apparatus of claim 1 wherein said treatment window is translucent.

12. The apparatus of claim 1 further comprising one or more optical sensor attached to the wall of said balloon.

13. An improved balloon catheter apparatus containing a defined treatment window for providing irradiation to a defined area, said improvement comprising using a reflective material to define the treatment window.

14. An improved balloon catheter apparatus containing a defined treatment window for providing irradiation to a defined area, said improvement comprising a fiber optic diffusion tip that is longer than said treatment window.

15. An improved balloon catheter apparatus containing a defined treatment window for providing irradiation to a defined area, said improvements comprising using a reflective material to define the treatment window and a fiber optic diffusion tip that is longer than said treatment window.

16. An improved method for administering light to a defined target area or for use with photodynamic therapy (PDT) said improvement comprising the use of a balloon catheter defined in claim 1.

17. The method of claim 16, wherein a laser diode of less than about 1.5 W is used a laser light source.

18. An improved method for administering light to a defined target area or for use with photodynamic therapy (PDT) said improvement comprising the use of a balloon catheter as defined in claim 6.

19. The method of claim 18, wherein a laser diode of less than about 1.5 W is used as a laser light source.

* * * * *